(12) United States Patent
Song et al.

(10) Patent No.: US 10,674,955 B2
(45) Date of Patent: Jun. 9, 2020

(54) SYSTEM AND METHOD FOR MONITORING THE HEALTH OF JOINTS

(71) Applicants: Gangbing Song, Pearland, TX (US); Yue Yu, New York, NY (US); Philip C. Noble, Houston, TX (US)

(72) Inventors: Gangbing Song, Pearland, TX (US); Yue Yu, New York, NY (US); Philip C. Noble, Houston, TX (US)

(73) Assignee: University of Houston, Houston, TX (US)

( * ) Notice: Subject to any disclaimer, the term of this patent is extended or adjusted under 35 U.S.C. 154(b) by 538 days.

(21) Appl. No.: 13/968,018

(22) Filed: Aug. 15, 2013

(65) Prior Publication Data
US 2014/0066812 A1    Mar. 6, 2014

Related U.S. Application Data

(60) Provisional application No. 61/683,476, filed on Aug. 15, 2012.

(51) Int. Cl.
*A61B 5/00* (2006.01)
*A61F 2/46* (2006.01)
*A61F 2/32* (2006.01)
*A61B 8/08* (2006.01)
(Continued)

(52) U.S. Cl.
CPC .......... *A61B 5/4528* (2013.01); *A61B 8/0858* (2013.01); *A61F 2/32* (2013.01); *A61F 2/468* (2013.01); *A61B 8/0875* (2013.01); *A61F 2002/30087* (2013.01); *A61F 2002/30673* (2013.01); *A61F 2002/481* (2013.01); *A61F 2002/488* (2013.01)

(58) Field of Classification Search
CPC .......... A61B 5/4528; A61B 17/320068; A61B 2017/0409; A61B 2562/028; A61B 5/1118; G01L 23/10; G01L 9/0052
USPC ....... 623/18.11; 600/587, 595, 590; 606/128
See application file for complete search history.

(56) References Cited

U.S. PATENT DOCUMENTS

| | | | |
|---|---|---|---|
| 2008/0065225 A1* | 3/2008 | Wasielewski | A61B 5/03 623/18.11 |
| 2008/0114309 A1 | 5/2008 | Zuckerman | |
| 2010/0262239 A1 | 10/2010 | Boyden et al. | |

(Continued)

OTHER PUBLICATIONS

CCoE Notice of Thesis Defense, Yue Yu, Presenter, Jul. 25, 2011.*
(Continued)

*Primary Examiner* — May A Abouelela
(74) *Attorney, Agent, or Firm* — Winstead PC

(57) ABSTRACT

A system and method for detecting lubrication conditions, lubrication regimes, impingement, stick-slip, and/or surface damage allows the health of a joint to be monitored. The system and method provides in situ or in vivo real-time monitoring of dynamic and static conditions of the joint. The monitoring system may use both passive and active sensing approaches that employ strategically placed piezoelectric transducers on/in the articulating components of the joint. In some embodiments, the transducers may be Lead Zirconate Titanate (PZT) transducers. Active sensing may be used to detect lubrication regimes under static and dynamic conditions. Passive sensing may be used to characterize the joint motion and abnormities, such as impingements and surface damages.

14 Claims, 15 Drawing Sheets

(51) Int. Cl.
A61F 2/48 (2006.01)
A61F 2/30 (2006.01)

(56) References Cited

U.S. PATENT DOCUMENTS

| | | | |
|---|---|---|---|
| 2010/0326187 A1* | 12/2010 | Stein | A61B 5/4528 73/379.01 |
| 2011/0066079 A1 | 3/2011 | Otto et al. | |
| 2011/0319755 A1 | 12/2011 | Stein et al. | |
| 2012/0191206 A1* | 7/2012 | Stein | A61B 5/01 623/20.32 |
| 2013/0066432 A1 | 3/2013 | Colwell, Jr. et al. | |

OTHER PUBLICATIONS

Affatato, S., Spinelli, M., Zavalloni, M., Leardini, W., and Viceconti, M. "Predictive role of the Lambda ratio in the evaluation of metal-on-metal total hip replacement." *Journal of Engineering in Medicine*, 2008: 617-628.

Amstutz, H. C., Campbell,P., and Le Duff Michel J. "Metal-on-metal hip resurfacing: what have we learned." *Instructional course lecture*, 2007: 149-161. Abstract Only retrieved from http://europepmc.org/abstract/MED/17472303.

Andrés, L. S. *Introduction to Pump Rotordynamics*. 2006.

Barrack, R. L. "Dislocation after total hip arthroplasty: implant design and orientation." *The Journal of American Academy of Orthopaedic Surgeons*, 2003: 89-99.

Bartz, R. L., Noble, P. H., Kadakia, N. R.,Tullos, H. S. "The Effect of Femoral Component Head Size on Posterior Dislocation of the Artificial Hip Joint." *The Journal of Bone & Joint Surgery*, 2000: 1300.

Bragdon, C. R., O'Connor, D. 0., Lowenstein, J. D.,Jasty, M., and Syniuta, W. D. "The importance of multidirectional motion on the wear of polyethylene." *Journal of Engineering in Medicine* 1989-1996 (vols. 203-210), 1996: 157-165.

Calonius, O., and Saikko,V. "Analysis of Polyethylene Particles Produced in Different Wear Conditions In Vitro." *Clinical Orthopaedics & Related Research*, 2002: 219-230. Abstract Only retrieved from http://journals.lww.com/corr/Abstract/2002/06000/Analysis_of_Polyethylene_Particles_Pr.

Dowson, D. "Tribological principles in metal-on-metal hip joint design." *Journal of Engineering in Medicine*, 2006: 161-171.

Dowson, D., and Jin, Z. M. "Metal-on-metal hip joint tribology." *Journal of Engineering in Medicine*, 2006: 107-118.

Dowson, D., Wang, F. C.,Wang, W. Z., and Jin, Z. M. "A predictive analysis of long term friction and wear characteristics of metal-on-metal total hip replacement." *Journal of Engineering Tribology*, 2007: 367-378.

Dwyer-Joyce, R. S, Drinkwater, B. W., and Donohoe, C. J. "The Measurement of Lubricant-Film Thickness Using Ultrasound." *Proceedings: Mathematical, Physical and Engineering Science*. The Royal Society, 2003. 957-976.

Girard, J., Lavigne, M., Vendittoli, P.A., and Roy, A.G. "Biomechanical reconstruction of the hip." *Journal of Bone and Joint Surgery*,2006: 721-726.

Gu, H., Song, G., Dhonde, H., Mo, Y. L. and Yan S. "Concrete early-age strength monitoring using embedded piezoelectric transducers." *Smart Materials and Structures*. 2006: 1837-45.

Hallab, Nadim, Merritt, Katharine, and Jacobs, Joshua J. "Metal Sensitivity in Patients with Orthopaedic Implants." *Journal of Bone and Joint Surgery*, 2001: 428-436.

Jin, Z. M. "Analysis of mixed lubrication mechanism in metal-on-metal hip joint replacements." *Journal of Engineering in Medicine*, 2002: 85-89.

Lu, Z., and McKellop, H. "Frictional heating of bearing materials tested in a hip joint wear simulator." *Journal of Engineering in Medicine*, 1997: 101-108.

MacDonald, S. J. "Metal-on-Metal Total Hip Arthroplasty: The Concerns." *Clinical Orthopaedics & Related Research*: the Hip Society Meeting, 2004: 86-93.

Malik, A., Maheshwari, A., Dorr, L. D. "Impingement with Total Hip Replacement." *The Journal of Bone & Joint Surgery*, 2007: 1832-1842.

Nevelos, J.E., Ingham, E., Doyle, C., Fisher, J., Nevelos, A.B. "Analysis of retrieved alumina ceramic components from Mittelmeier total hip prostheses." *Biomaterials*, 1999: 1833-1840.

Pylios, T. and Shepherd, D. E. T. "Prediction of lubrication regimes in wrist implants with spherical bearing surfaces." *J Biomechanics*, 2004: 405-411.

Ravikiran, A. "Wear Quantification." *Journal of Tribology*, 2000: 650-656.

Shon, W. Y., Baldini, T., Peterson, M. G., Wright, T. M., and Salvati, E. A. "Impingement in Total Hip Arthroplasty: A Study of Retrieved Acetabular Comgonents." The Journal of Arthroplasty, 2005: 427-435.

Siebenrock, K.A., Kalberrnatten, D.F ., Ganz, R .. "Effect of pelvic tilt on acetabular retroversion: a study of pelves from cadavers." Clinical Orthopedic Related Research. 2003; 407:241-8. Abstract Only retrieved from http://www.ncbi.nlm.nih.gov/pubmed/12567152.

Sieber, H.P., Rieker, C. B., and Kottig, P. "Analysis of 118 second-generation metal-on-metal retrieved hip implants." *The Journal of Bone Joint Surgery*, 1999: 46-50.

Song, G., Gu, H. and Mo, Y. L. "Smart aggregates: multi-functional sensors for concrete structures—a tutorial and a review." *Smart Materials and Structures*. 2008:033001.

Song, G., Mo, Y. L., Otero, K. and Gu, H. "Health monitoring and rehabilitation of a concrete structure using intelligentmaterials" *Smart Materials and Structures*. 2006:309-314.

Tanino, H., ItoH, Harman, Melinda, K., Matsuno, Takeo, H., Andrew, W. and Banks, Scott, A. "An in Vivo Model for Intraoperative Assessment of Impingement and Dislocation in Total Hip Arthroplasty." *The Journal of Arthroplasty*, 2008: 714-720.

Udofia, I. J., and Jin, Z. M. "Elastohydrodynamic lubrication analysis of metal-on-metal hip-resurfacing prostheses." *Journal of Biomechanics*, 2003: 537-544.

Unsworth, A., Vassiliou, K., Elfick, A. P. D., Scholes,S. C., McMinn, D., and Band, T. "Fluid-film lubrication of metal-on-metal hip joints-fact or fiction." *The International Society for Technology and Arthroplasty Meeting*. San Francisco, California, USA, 2003. 24-27. Abstract Only retrieved from http://pih.sagepub.com/content/220/2/161.abstract.

Wang, F. C., Brockett, C., Williams, S., Udofia, I., Fisher, J., and Jin, Z. M.,. "Lubrication and friction prediction in metal-on-metal hip implants." *Physics in Medicine and Biology*, 2008: 1277-1293.

Wang, F. C., and Jin, Z. M. "Lubrication modeling of artificial hip joints." In Solid Mechanics and its Applications, by R. W. Snidle and H. P. Evans,2006: 385-396.

Williams, S., Stewart, T.D., Ingham, E., Stone, M.H. and Fisher, J. "Metal-on-metal bearing wear with different swing phase loads." *J. Biomed Mater Res B Appl Biomater*. 2004: 233-9.

Yu, Y. Monitoring of Metal-on-Metal Hip Prosthesis Lubrication Using PZT Transducers. Thesis Defense presented at the University of Houston on Jul. 29, 2011.

* cited by examiner

Mixed lubrication

Border of mixed and boundary

Boundary lubrication

FIG. 17F
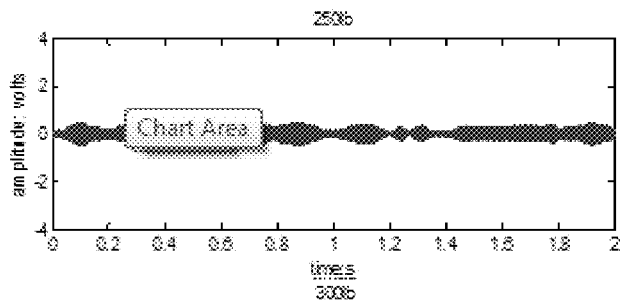
FIG. 17G
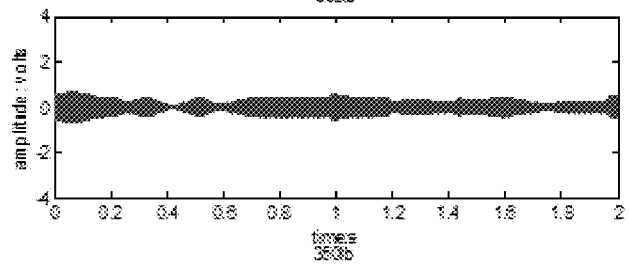
Decreasing Lambda Ratio
FIG. 17H
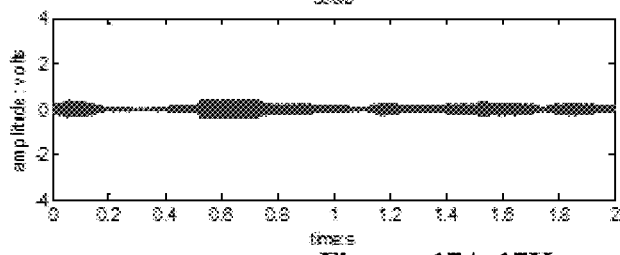
Boundary Lubrication
Figures 17A-17H
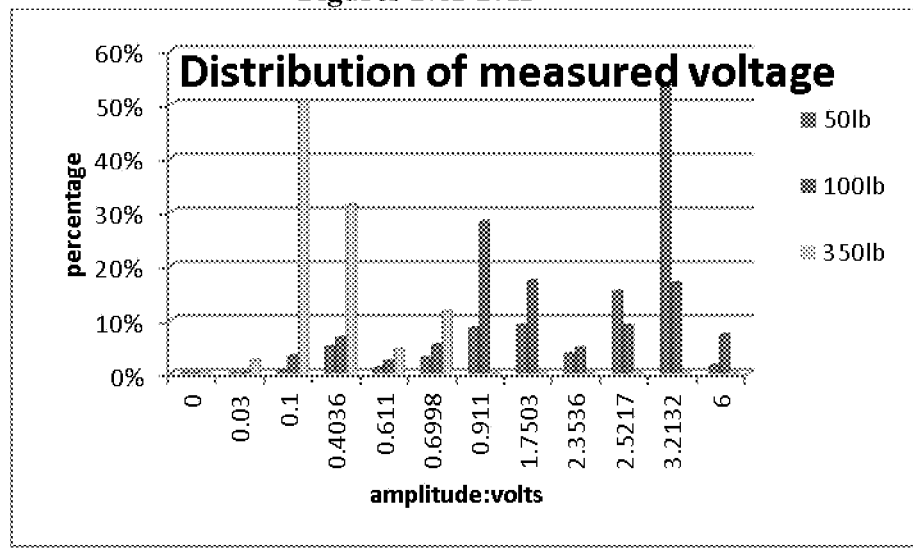
Figure 18

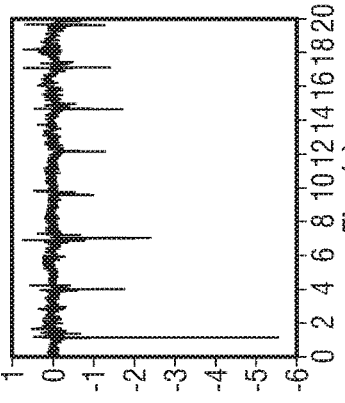
FIG. 25
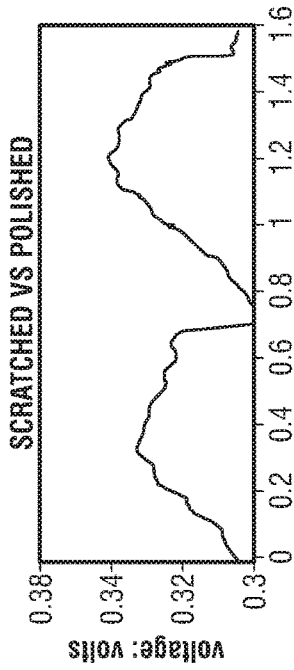
FIG. 26C
FIG. 26A
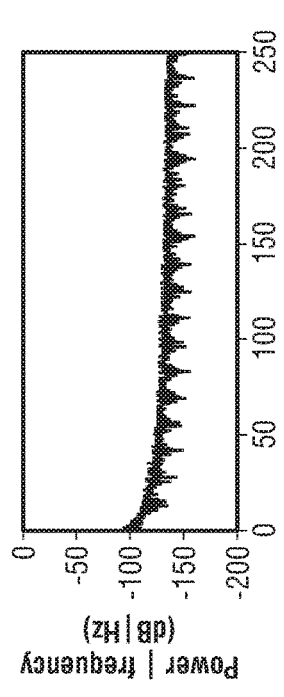
FIG. 26D
FIG. 26B

SYSTEM AND METHOD FOR MONITORING THE HEALTH OF JOINTS

RELATED APPLICATIONS

This application claims the benefit of U.S. Provisional Patent Application No. 61/683,476, filed on Aug. 15, 2012, which is incorporated herein by reference.

STATEMENT REGARDING SPONSORED RESEARCH

This invention was made with government support under Grant No. W81XWH-0920139 awarded by the U.S. Army Medical Research and Material Command. The government has certain rights in the invention.

BACKGROUND OF INVENTION

Arthroplasty surgery is currently the most reliable and successful orthopedic treatment for osseous joint failure due to arthritis pain or severe physical joint damage. In the USA, around 200,000 patients receive hip replacement surgeries each year. Similar surgical procedures are performed also on other joints, including shoulders, elbows and knees. The articulating surfaces of the artificial joint prosthesis are commonly fabricated from three combinations of bearing materials: (i) ultra-high molecular weight polyethylene articulating against a metal (or ceramic) femoral head replacement (i.e. a metal on plastic (MOP) couple), (ii) a metal-on-metal (MOM) couple, or (iii) a ceramic-on-ceramic (COC) couple. MOM and COC articulations function with minimal wear and acceptable frictional resistance because of the presence of a thin layer of joint fluid which is held within the narrow space between the two highly polished counterfaces. This fluid layer keeps the surfaces apart and prevents direct contact between the metal-metal or ceramic-ceramic surfaces.

However, under some circumstances, the two counterfaces may come into contact due to loss of fluid over a focal area, or to increased roughening of the surface(s). When this occurs the lubrication of the bearing is said to have failed and wearing of the metal or ceramic surfaces will occur. A second form of unintended contact between the counterfaces occurs when the articulating components are rotated beyond their physical limits, leading to "impingement" or physical contact between the non-articulating surface of one component and the surface (articulating or non-articulating) of the other component. One example is a collision between the neck of the femoral component, directly below the modular head and the rim of the acetabular cup. This form of contact occurs when the patient places the femur in a position which exceeds the articulating range of motion (ROM) of the artificial joint. A third form of unintended contact leading to adverse wear of the artificial joint occurs when the head of the prosthesis is displaced from the center of the mating acetabular counterface. This can occur during joint motion and is often seen to cause the femoral head to "ride up" the lateral edge of the acetabular bearing, with loss of contact between the articulating surfaces over all but a small area. This form of motion is termed "micro-separation" and leads to high contact stresses and accelerated bearing wear.

The microscopic particles generated by the wear of artificial joint can lead to series inflammatory reactions, chronic pain, and permanent disability. In advanced cases, where this disease process has been left undetected, devastating loss of nerve and muscle tissue may occur, in addition to sensitization of the patient to metallic ions within the implanted devices, most notably cobalt. Additionally, concerns exist regarding hypersensitivity, increased incidence of instability, and pathologic changes ranging from dementia to chromosomal abnormalities. Thus, it is imperative to develop a detection method to help patients and physicians quickly diagnose the occurrence of lubrication degradation and impingement.

Although there has been a large amount of research in alternative methods to estimate or measure the thickness of lubrication and to identify lubrication regimes, most systems have astonishingly high requirements for the testing signals and are limited for in vitro tests only. The systems and methods discussed herein allow in situ or in vivo, real-time monitoring of both the lubrication and the structural health of MOM artificial joints. The systems and methods disclosed herein provides a real time, more feasible, and lower cost alternative that helps better characterize and understand the features of degradation of lubrication and other negative scenarios, thereby allowing physicians to quickly diagnose the structural health of joints or implants, thus prolonging the active time of the implants and reducing the chance of needing a revision surgery.

SUMMARY OF THE INVENTION

In one embodiment, a system for monitoring a joint is provided. The system for monitoring the joint may include a joint with a first articulating component, and a second articulating component positioned on said first articulating component, wherein said second articulating component is capable of rotating relative to said first articulating component. The system may also include a first piezoelectric transducer positioned at a first end of said joint, wherein said first piezoelectric transducer detects acoustic signals. In some embodiments, a second piezoelectric transducer positioned at a second end opposite said first end, wherein said second piezoelectric sensor is capable of generating desired acoustic signals. The system may utilize detected signals to determine lubrication conditions of the joint, such as, but not limited to, lubrication thickness, lubrication regime, stick-slip, impingement, surface damage or combinations thereof.

In another embodiment, a method for monitoring a joint includes positioning a first piezoelectric transducer near a joint, wherein the first piezoelectric transducer is capable of detecting acoustic signals. The first piezoelectric transducer may monitor the joint to detect passive signals generated by the joint. The passive signals may be analyzed to determine lubrication conditions of the joint.

In yet another embodiment, a method for monitoring a joint includes positioning first and second piezoelectric transducers near the joint, wherein the first piezoelectric transducer and the second piezoelectric transducer are separated by a lubrication region. A voltage may be applied to the second piezoelectric transducer, wherein the applied voltage causes the second piezoelectric transducer to generate acoustic signals. The acoustic signals may propagate through the joint from the second piezoelectric transducer to the first piezoelectric transducer, and the received signals at the first piezoelectric transducer may be analyzed to determine lubrication conditions of the joint.

The foregoing has outlined rather broadly various features of the present disclosure in order that the detailed description that follows may be better understood. Additional features and advantages of the disclosure will be described hereinafter.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein:

FIGS. 17A-17H illustrate sensor signals among different lubrication regimes;

FIG. 18 illustrates distribution of measured amplitude with regards to different loading;

FIG. 25 illustrates detection of impingement; and

FIGS. 26A-26D illustrate surface damage detection.

DETAILED DESCRIPTION

Figure 1:
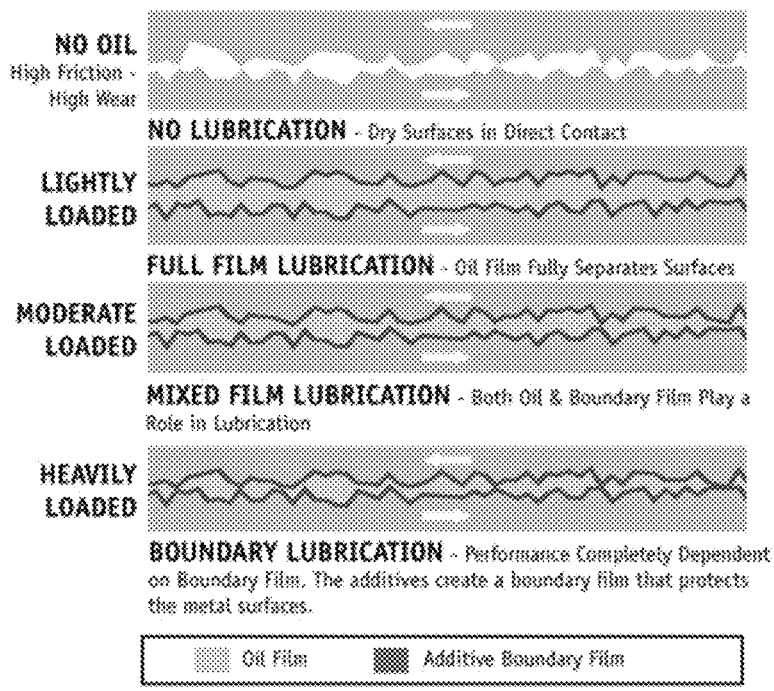
FIG. 1 is an illustration of classifications of lubrication regimes.

Refer now to the drawings wherein depicted elements are not necessarily shown to scale and wherein like or similar elements are designated by the same reference numeral through the several views.

Referring to the drawings in general, it will be understood that the illustrations are for the purpose of describing particular implementations of the disclosure and are not intended to be limiting thereto. While most of the terms used herein will be recognizable to those of ordinary skill in the art, it should be understood that when not explicitly defined, terms should be interpreted as adopting a meaning presently accepted by those of ordinary skill in the art.

It is to be understood that both the foregoing general description and the following detailed description are exemplary and explanatory only, and are not restrictive of the invention, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise.

NOMENCLATURE c radial clearance, $R_2-R_1$
$c_d$ diametral clearance
d cup thickness, $R_3-R_2$
e modulus of elasticity
E' equivalent modulus of elasticity
h total film thickness
$h_{min}$ minimum lubricant film thickness
$H_{min}$ non-dimensional film thickness, $h_{min}/R$
Lp peak load (N)
P pressure
R bearing radius (m)
$R_e$ effective radius for the ball-on-plane model, $$R = \frac{R_1 R_2}{C}$$

$R_1$ femoral head radius
$R_2$ cup radius
$R_3$ outside radius of the cup
$T_t$ true torque
$T_f$ frictional torque measured in the forward direction
$T_r$ frictional torque measured in the reverse direction
U non-dimensional velocity for the ball-on-plane model
w applied load in the vertical direction
W non-dimensional load for the ball-on-plane model
δ elastic deformation
η viscosity of synovial fluid
v relative velocity of two articulation surfaces
ω angular velocity
μ coefficient of friction
$v_m$ the velocity of acoustic wave propagating in materials m
z' acoustic impedance of identical materials on both side Systems and methods for monitoring the health of joints are discussed herein. In particular, the systems and methods may monitor and detect lubrication conditions, lubrication degradation, lubrication regimes, impingement, stick-slip, micro-separation, surface damage, structural health or combinations thereof for joints. The systems and methods disclosed herein provide an in situ or in vivo, real-time, feasible, and a lower cost monitoring that helps characterize and understand the features of degradation of lubrication and other scenarios affecting the longevity of a joint. The joint may be an artificial joint, natural joint or diseased joint. The systems and methods may use a piezoelectric sensor to detect lubricant thickness and identify the different lubrication regimes in both static and dynamic conditions. Some embodiments may utilize active sensing to identify lubrication regimes. Some embodiments may utilize passive sensing to characterize joint movement. The systems and methods providing monitoring of artificial joints may allow the active time of implants to be prolonged and reduce the chance of revision surgeries in patients.

For the purposes of illustration, the joints specifically discussed herein are artificial hip joints. However, it will be recognized that the systems and methods may also be applied to knee joints (including the articulation of the patella and distal femur, elbow joints, shoulder joints, temporo-mandibular joint (jaw) or any other joints. Further, the joints may be artificial joints, natural joints or diseased joints. In some embodiments, the joint monitored may be the joint formed by an acetabular of a pelvis and greater trochanter of a femur. In some embodiments, the joint monitored may be the joint formed by a trochlear notch of an ulna and trochlea of a humerus. In some embodiments, the joint monitored may be the joint formed by condyles of a tibia and condyles of a femur. In some embodiments, the joint monitored may be a glenohumeral joint formed by a glenoid cavity of the scapula and a humeral head of the humerus.

Hip arthroplasty, one of the most commonly performed surgeries in the world, involves the repair of the hip joint by replacing damaged surfaces with prosthetic implants. Such implants face serious problems during their lifetime due to the wear induced degradation. Wear is a serious problem from the viewpoint of the biocompatibility of the particulate debris as well as the mechanical endurance of the bulk materials. Wear rate increases greatly when lubrication degradation and impingement occur, probably caused by multiple reasons including the patients' activity levels and range of motion. Thus, methods to alleviate the wear-induced complications are critically important.

Impingement Degradation

Impingement involves the harmful mechanical abutment from bone-to-bone or metal-to-metal contact, such as between a metal femoral neck and the cup liner of an artificial hip. Impingement is responsible for rim and bony wear, and results in a series of potential adverse consequences including accelerated loosening of the implant and liberation of metal debris from the femoral neck, which potentially increases the risk of osteolysis, subluxation and dislocation. The principles regarding impingement in the natural osseous hip are similar in concept to what can occur in the prosthetic hip. Taking a total hip replacement as an example, impingement involves the harmful mechanical abutment between the metal femoral neck and the cup liner. Impingement is influenced by prosthetic design, component position, biomechanical factors and patient variables. On the other hand, while a few potentially deleterious factors could be prevented by an improved prosthetic design or an accurate surgery, patient-related variables are inevitable. For example, in some case, an abnormal degree of pelvic tilt occurs in some patients as a result of the static pelvic position on the operating table relative to the dynamic pelvic position during activities. Impingement is responsible for not only material loss and release of debris, but also breakdown of hydrodynamic lubrication, loosening of the implant and separation of components. Moreover, because impingement is a dynamic process, it has been difficult to identify and define its prevalence on the basis of clinical evaluations or plain radiographs. There are no radiographic techniques with which to validate the occurrence of impingement. So far the main resort for impingement analysis is to perform retrieval studies on failed implants.

Wear and Lubrication of MOM and COC Bearings

In hard-on-hard bearings (MOM and COC), localized loss of fluid lubrication leads to a dramatic increase in wear of the articulating counterfaces. The excellent tribologic performance of MOM bearings, as evidenced by extremely low wear rates (e.g. 2-20 μm/year), is heavily dependent upon maintenance of hydrodynamic lubrication at the articulating surfaces. This requires that the fluid film separating the joint surfaces be maintained under the cyclic conditions present during walking and other activities in which dynamic loads and motions characterize normal implant function.

Fluid lubrication theory teaches that when a rigid convex surface moves with respect to a mating concave surface under load in the presence of a lubricating fluid, several distinct modes, or regimes of lubrication may be present. These modes arise through the interaction between: (i) the inherent roughness of every bearing surface, no matter how finely polished. This roughness is comprised of local peaks (asperities) and valleys, (ii) the lubricant layer, particularly its thickness and viscosity, and (iii) the load and relative velocity of the articulating surfaces.

Common modes or regimes of lubrication in rotating bearings are:

1. Fluid film lubrication: In this regime there is no contact between the articulating surfaces, and all of the applied load passing across the joint is supported by the interspersed layer of lubricant fluid. As loading of the joint causes pressure within the fluid which acts to force it out of the joint, the lubricant within the joint must be maintained with either an external pressure source (Hydrostatic Lubrication), or by relative movement of the surfaces and the viscous resistance of the fluid, (Hydrodynamic lubrication).

2. Partial or mixed lubrication regime: The fluid film is not thick enough compared to the roughness of the bearing surfaces to prevent the tallest asperities from protruding through the film. As the surfaces move relative to each other there is occasional metal-metal or ceramic-ceramic contact causing increased friction and wear. Under higher loads or with deformable surfaces, elastic deformation of the asperities can enlarge the loadbearing area, leading to mixed load transfer via both contact points and the viscous lubricant film (Elasto-hydrodynamic lubrication).

3. Boundary lubrication: When the thickness of the lubricant film decreases, contact between the asperities is more frequent and friction and wear increase. Heat developed by the stick-slip of the contacting surfaces elevates the temperature at the surface and chemical reactions may occur between the lubricant and the contact surface, leading to the formation of a highly tenacious layer or film (boundary film), on the moving solid surfaces which is capable of supporting the load, while allowing relative sliding between the counterfaces.

4. Dry Contact: When no lubricant is present between the two surfaces, contact occurs at their asperities. Under high local pressures and temperatures, welding of metal may occur with pull-out of individual grains or attached fragments of each counterface during initiation of sliding. This leads to rapid and catastrophic wear and material loss. A diagram of different regimes of lubrication is shown in FIG. 1.

Studies show that when the thickness of the lubricant reaches a low level, approximately 20 nm for MOM prosthesis, the wear rate, both in running in the bearing, and under steady-state conditions overwhelmingly increase.

Methods to Calculate the Thickness of the Lubricant Layer

In the field of tribology, methods are available for predicting the thickness of fluid films formed between surfaces based on Reynolds's equation which has been derived for the analysis of lubricated contacts in seals, synovial joints and elastomeric bearings. The minimum thickness of lubricant layer ($h_{min}$) can be predicted from the diameter of the bearing (d), the viscosity of the lubricant ($\eta$), the relative angular velocity of the counterfaces ($\Omega$), the load applied, and the effective elastic modulus are known as shown in, $$h_{min} = 1.40 \frac{d^2}{c_d} \left( \frac{\eta \Omega c_d}{2E'd} \right)^{0.65} \left( \frac{4wc_d^2}{E'd^4} \right)^{-0.21}. \quad (2\text{-}1)$$

Methods to predict the minimum thickness of the lubrication film under elastohydrodynamic lubrication (EHL) conditions were developed from a ball-on-plane model.

The thickness of a layer separating two articulating surfaces may be determined by passing ultrasound waves through the layer and measuring the time difference between the signal transmitted through the layer and reflected back, and the signal immediately reflected at the boundary of the layer and the first counterface. This is called "time-of-flight method." For multiple layers, the thickness can be calculated by the time difference between the corresponding sequences of the reflected signals, as described by $$h = \frac{t_2 - t_1}{2} v_m. \quad (2\text{-}2)$$

However, the ultrasound method has some limitations. The propagation distance must be greater than the pulse width in order to distinguish between two reflected pulses. This means that for a typical frequency of around 50 MHz, the method is capable of measuring film thicknesses greater than 40 μm.

Additionally, a film-resonance method has proven capable of measuring film thicknesses down to 10 μm, however, this is still far in excess of the film thicknesses encountered in MOM and COC joint replacements within the body which are of the order of 20-200 nm, two orders of magnitude thinner. In addition, this method is highly dependent on the signal-noise ratio and the properties of lubricant. Thus, it is not suitable for implantation.

Method for Determining the Regime of Lubrication

Two different methods have been developed to determine which lubrication regime is present in lubricated bearings, based on calculation of the lambda ratio or the coefficient of friction. However, as these calculations are based on key parameters that are difficult to measure under in vivo conditions, these methods have been limited to use in vitro, often in the research setting.

Lambda Ratio

A dimensionless parameter, the "lambda ratio" ($\lambda$), is defined as the ratio between the minimum lubricant thickness and the average roughness (RMS) of the two articulating surfaces.

$$\lambda = \frac{h_{min}}{\sqrt{(R_a)_{head}^2 + (R_a)_{cup}^2}}, \quad (2\text{-}4)$$

where $$[(R)_a]_{composite} = \sqrt{(R_a)_{head}^2 + (R_a)_{cup}^2}. \quad (2\text{-}5)$$

The lambda ratio is used in tribology and is able to distinguish between regimes of lubrication, as shown in Table 1.

TABLE 1

Regime of Lubrication vs. Lambda Ratio

| Regime of lubrication | Range of lambda ratio |
| --- | --- |
| Hydrodynamic | $\lambda > 3$ |
| Partial/Mixed | $1 < \lambda < 3$ |
| Boundary | $\lambda < 1$ |

Although the exact values of the lambda ratio corresponding to each regime may vary slightly with different lubricants or articulation conditions, boundary lubrication is always considered to occur for values of the lambda ratio less than 1.

The lambda ratio has been applied to select parameters for the design of hip prostheses to obtain low friction and wear rates under a broad range of conditions. Using this formulation, it is possible to examine the effect of parameters including the diametral clearance, the shell thickness, the surface roughness of hip bearings of a given radius on the minimum lubricant thickness, and hence the wear rate of the implant.

Coefficients of Friction

Figure 2:
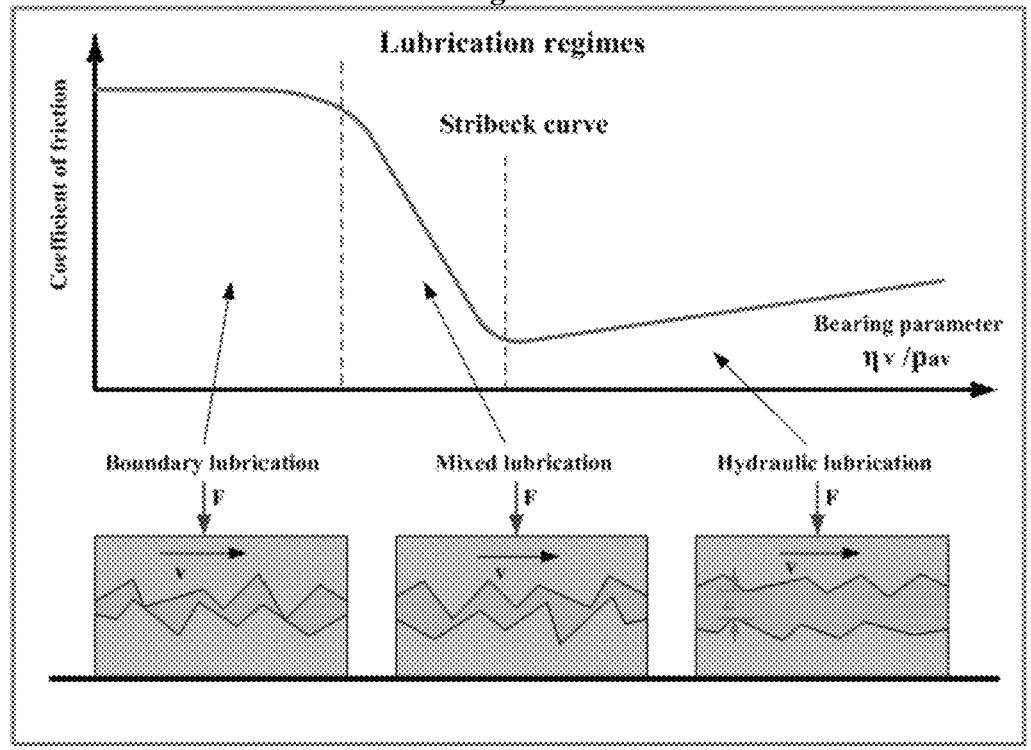
FIG. 2 is an illustration of a Stribeck curve and lubrication regimes.

The lubrication regime may also be deduced from the relationship between the friction coefficient and a dimensionless lubrication parameter $\eta \Omega / w$, where $\eta$ is the fluid viscosity, $\omega$ is the angular velocity of the bearing surfaces, and w is the vertical load supported by the bearing. The graphical representation of this relationship is referred to as the Stribeck curve, which depicts regions corresponding to the boundary, mixed and fluid-film lubrication regimes, is shown in FIG. 2. When motion of a lubricated bearing first commences, fluid is drawn into the articulating interface, causing the surfaces to separate. This leads to the onset of mixed lubrication, characterized by a sharp drop in the coefficient of friction due to the reduction in contact between surfaces and the increasing area and thickness of the interposed fluid layer. The surfaces continue to separate due to 1) the increase of viscosity, 2) the increase of speed or 3) the decrease of loading until there is a full fluid film without mutual surface contacts. The friction coefficient reaches its minimum at the transition from mixed lubrication to hydraulic (hydrodynamic) lubrication.

The Piezoelectric Effect

Piezoelectric solids possess the physical property of generating a potential gradient in response to deformation (the direct piezoelectric effect). This property can also operates in reverse (the converse piezoelectric effect), in that the application of a voltage across of the same solid causes it to expand or contract. This phenomenon can be expressed in terms of the following equations:

$$D = d'T + \varepsilon^T E, \quad (3\text{-}1)$$

$$S = s^E T + dE \quad (3\text{-}2)$$

where D is the electric displacement, S is strain, s is the compliance of medium, $\varepsilon$ is the permittivity of the medium, d represents the piezoelectric constants, the superscript E indicates a zero, or constant, electric field; the superscript T indicates a zero, or constant, stress field, and the superscript T represents transpose of a matrix or vector.

Figure 3:
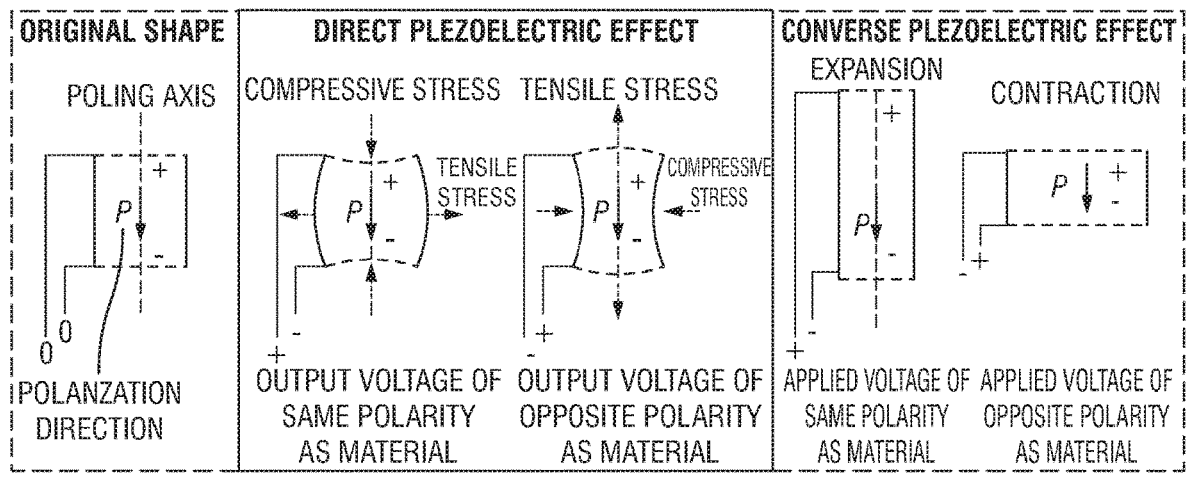
FIG. 3 is an illustration of direct and converse piezoelectric effects.

As described in equation (3-1), materials exhibiting the direct piezoelectric effect could function as a sensor, whereas those exhibiting the converse piezoelectric effect (equation 3-2) could function as an actuator, as shown in FIG. 3.

A non-limiting example of a piezoelectric material, lead zirconate titanate (PZT) is discussed herein, which is a ceramic perovskite material that shows a remarkable piezoelectric effect. In other embodiments, the piezoelectric material may be quartz barium titanate or lead niobate. PZTs have a strong piezoelectric effect and high Curie point, as well as a wide range of properties available by simply making changes in composition. The following advantages are possessed by PZT:

1. Repeatable nanometer and sub-nanometer sized steps can be achieved with piezoelectric devices because they derive their motion through solid state crystal effects. There are no moving parts (no "stick-slip" effect).

2. Piezoelectric devices can be designed to move heavy loads (several tons) or can be made to move lighter loads at high frequencies.

3. Piezoelectrics act as a capacitive load and require very little power in static operation, simplifying power supply needs.

4. Piezoelectric devices require no maintenance because they are solid state and their motion is based on molecular effects within the ferroelectric crystals.

Important Piezoelectric Constants

Physical constants, such as the elasticity and the permittivity of piezoelectric materials, are tensor quantities that vary with both the directions of the applied stress and the electric field. For this reason, the constants are generally given two subscript indices which refer to the direction of the two related quantities (stress and electric field). A superscript index is used to indicate a quantity that is kept constant.

The piezoelectric charge constant, $d_{ij}$, is defined as the electric polarization generated in a material per unit mechanical stress applied to it. The first subscript refers to the direction of polarization generated in the material (at E=0) or to the applied field strength; the second refers to the direction of the applied stress or to the direction of the induced strain.

For example, $d_{33}$: The induced polarization per unit applied stress in direction 3. Alternatively it is the induced strain per unit electric field in direction 3.

$d_{31}$: The induced polarization in direction 3 per unit stress applied in direction 1. Alternatively it is the mechanical strain induced in the material in direction 1 per unit electric filed applied in direction 3.

The piezoelectric voltage constant, $g_{ij}$, is defined as the electric field generated in a material per unit mechanical stress applied to it. The first subscript refers to the direction of the electric field generated in the material or to the applied electric displacement; the second refers respectively to the direction of the applied stress or to the direction of the induced strain.

For example:

$g_{31}$: The induced electric field in direction 3 per unit stress applied in direction 1. Alternatively it is the mechanical strain induced in the material in direction 1 per unit electric displacement applied in direction 3.

$g_{15}$: The induced electric field in direction 1 per unit shear stress applied about axis direction 2. Alternatively it is the shear strain induced in the material about axis 2 per unit electric displacement applied in direction 1.

Sensing Strategy

As piezoelectric materials may be used as sensors to record vibration signals, and as actuators to generate a wide range of vibrations. In some embodiments, one or more piezoelectric transducers may be utilized as sensors or actuators to provide a complete inspection for structural health monitoring of an implant.

Passive Sensing

In terms of energy, passive sensing measures energy that is naturally available. Passive sensors, therefore, can be used to detect incoming energy. For example, a hip motion simulator may cause a pendulum and DC motor to drive a ball moving relative to an acetabular socket. Since the acetabulum is not completely smooth or rigid, static deformation and also vibrations occur due to abrasion and non-uniform loading. Such vibration is large enough for a piezoelectric sensor to detect. Thus, passive sensing may be utilized to capture and compare the vibration signals of implant pairs with differing levels of surface roughness.

Active Sensing

Figure 4A:
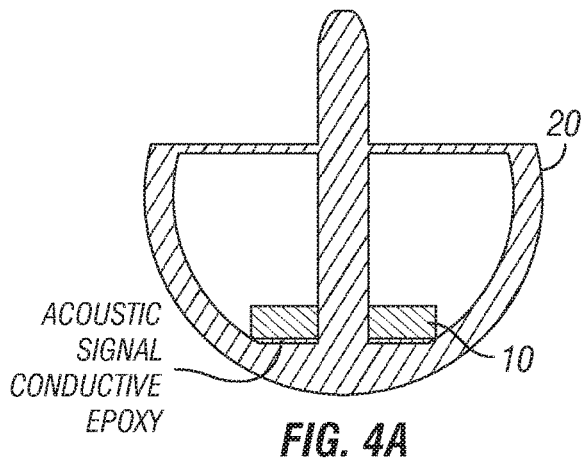
FIGS. 4A-4C are an illustrative embodiment of a system for monitoring an artificial joint.
Figure 4B:
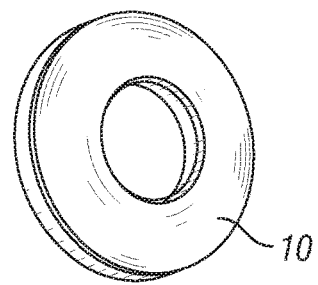
Figure 4C:
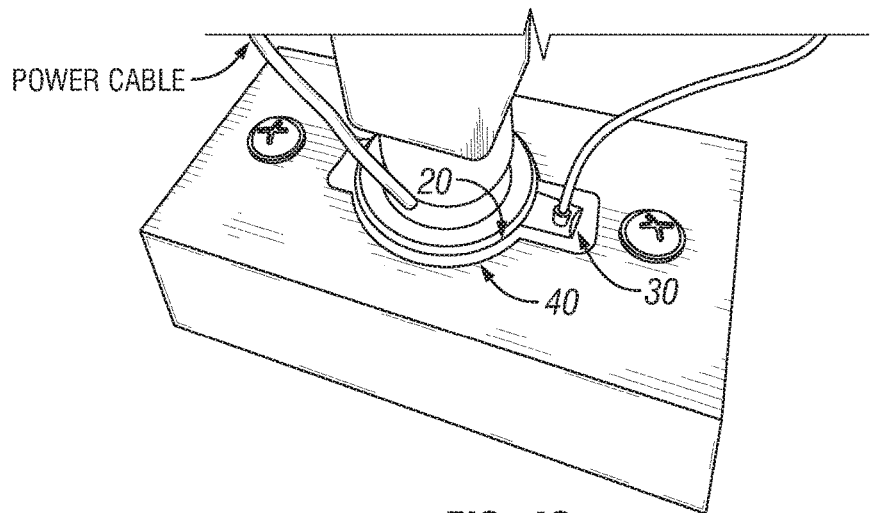

Active sensing utilizes an energy source for wave propagation. For example, a transducer may emit radiation or other forms of energy which is directed toward the target. In some embodiments, two piezoelectric transducers utilized active sensing, one sensor and one actuator. In other embodiments, one transducer can be used to both send out and pick up the reflected signal. In some embodiments, a piezoelectric transducer 10 utilized as an actuator may be mounted in a ball 20, and another piezoelectric transducer 30 may be mounted on the exterior edge of a socket or cup 40 as a sensor in an artificial joint, as shown in FIGS. 4A-4C. A signal or function generator (not shown), which is able to generate sine wave and sweep signal, such as with a frequency up to 15 MHz, may be connected to the actuator to produce acoustic or ultrasonic signals. The second piezoelectric transducer 30, acting as an acoustic emission sensor, may be positioned near a ball 20. For example, the acoustic emission sensor may be a cylindrical acoustic emission sensor with a diameter of 10 mm and a height of 12 mm. A core of the sensor is also a piezoelectric patch which is delicately coated and packaged. In some embodiments, the sensor may be calibrated and decoupled with peak sensitivity (Ref V/µBar) of more than 65 dB. In some embodiments, the operating frequency of the sensor is from 100 KHz to 400 KHz.

Figure 5:
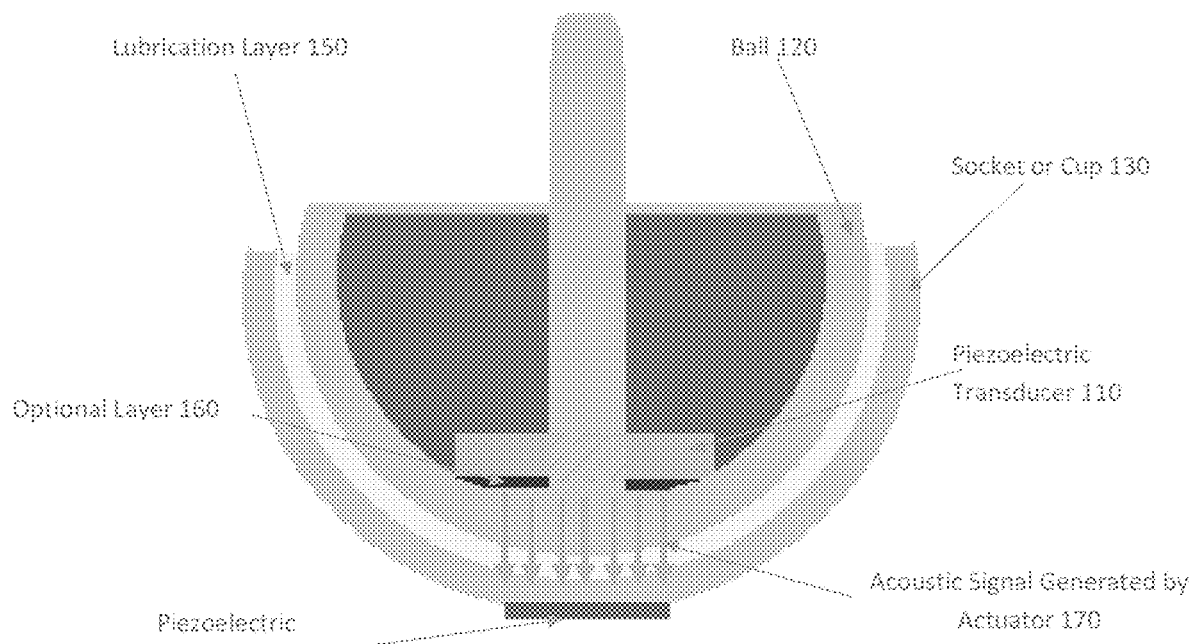
FIG. 5 is an illustrative embodiment of the propagation of an acoustic signal through a system for monitoring an artificial joint.

Since repeatable nanometer and sub-nanometer sized steps at high frequency can be achieved with some piezoelectric materials, it can be considered that the waveform and frequency of the transmitted wave is approximately identical to those of the generated signal, only in another form of energy. The transmitted wave will pass through layers of materials to reach the sensors, such as a wall of the ball, the lubricant or the air between the surface gap, and the wall of the socket, as shown in FIG. 5. Due to the differences in the path of the propagation of acoustic waves within air and the lubricant, the captured energy varies considerably between the two mediums. The signal or energy received by the sensor may be utilized to determine whether the gap between the ball the socket is filled with lubricant or not. Furthermore, the received energy also differs with different thicknesses of the lubricant layer, which allows the thicknesses of the lubricant layer to be determined.

As the frequency range of interest for active sensing it is quite different from that of the signals generated in passive sensing, it is easy to distinguish the two. In some embodiments, an acoustic emission sensor may be employed for active sensing with an operating frequency range from 100 KHz to 300 KHz. This allows a low frequency signal to be combined with the transmitted signal to minimize interference with active sensing.

Structural Health Monitoring with Piezoelectric Transducers

In the systems and methods for monitoring the health of joints, a piezoelectric sensor may be utilized to monitor and detect changes in frictional conditions within the articulation, lubrication regimes, impingement, micro-separation and structural health. As a nonlimiting example, a piezoelectric sensor may be a Lead Zirconate Titanate (PZT) transducer, which is a kind of ceramic perovskite material that possesses a strong piezoelectric effect. The advantage of a piezoelectric transducer lies in its capability of being used as both a sensor and an actuator. Piezoelectric sensors are sensitive to vibration while piezoelectric actuators are able to move heavy loads of more than several tons. Both the sensors and the actuators have a wide range of operating frequency, which renders them qualified for working in a frequency less than 1 Hz or higher than 10 MHz.

Due to dual functionality and high energy density, a piezoelectric transducer can be fabricated in a small size, and thus is easy to place in artificial joints. For example, piezoelectric transducers may be embedded in and/or mounted on any structure for active and passive sensing. In active sensing, a piezoelectric transducer may be used as an actuator, and transmits a designed wave. Another piezoelectric transducer may be used as a sensor to capture the signal after the wave propagates through a medium. Since the behavior of the waves is influenced by the properties and the thickness of the medium, lubrication regimes and any damage or unexpected change along the path the wave travels can be detected. In passive sensing, which may not require an external power supply, signals may be collected in real-time, and when analyzing the differences among captured signals, the changes in structures can be reflected.

In some embodiments, a first piezoelectric transducer may be positioned at a first end of an artificial joint. A second piezoelectric transducer may be positioned at second end of the joint opposite the first end. The first piezoelectric transducer may act as an actuator that is capable of generating an acoustic signal. The acoustic signal may pass through components of an artificial joint and a lubrication layer between the first and second piezoelectric transducers. The second piezoelectric transducer may act as a sensor receiving the acoustic signal. The acoustic signal varies as it propagates through the artificial joint and lubrication layer to the second piezoelectric transducer. An analysis of a received acoustic signal captured by the second piezoelectric transducer may be utilized to monitor and detect changes in frictional conditions within the articulation, lubrication regimes, impingement, the occurrence of stick-slip motion, surface damage and structural health. Both the active and passive sensing approaches may be employed for the monitoring of the lubrication regimes and the structural health of the implant.

In some embodiments, piezoelectric transducers may be embedded in or mounted on a femoral head and acetabular socket of a hip prosthesis. In some embodiments, piezoelectric transducers may be embedded in or mounted on the femoral and tibial components of a knee prosthesis. In some embodiments, piezoelectric transducers may be embedded in or mounted on the humeral and ulnar components of an elbow prosthesis. In some embodiments, piezoelectric transducers may be embedded in or mounted on a glenoid and humeral components of a shoulder prosthesis. Both the active and passive sensing approaches may be employed for the monitoring of the lubrication regimes and the structural health of the implant.

FIG. 5 is an illustrative example of a system for monitoring an artificial joint. An artificial joint may provide articulating components, such as a ball 120 and cup or socket 130, separated by a lubrication layer 150. It should be noted that a ball as referenced herein may be any curve shaped portion of a joint that is received by a cup or socket. As nonlimiting examples, articulating components may be a femoral head or condyles of a femur, trochlea of a humerus, humeral head, an acetabular socket of the pelvis, the tibial component of a knee prosthesis, the ulnar component of an elbow prosthesis, or the glenoid cavity of a shoulder prosthesis. In order to monitor the artificial joint, one or more piezoelectric transducers 110, 140 may be positioned in the artificial joint.

In an active sensing mode, a one piezoelectric transducer 110 may act as an actuator. Actuation of piezoelectric transducer 110 may generate an acoustic signal 170 that is propagated through optional layer 160, ball 120, lubrication layer 150, and cup 130. In some embodiments, piezoelectric transducer 110 may be optionally coupled to a signal or function generator (not shown). The signal generator may be capable of generating a sine wave and sweep signal to aid in producing acoustic and/or ultrasonic signals. The energy of acoustic signal 170 changes as it passes through the various materials. Piezoelectric sensor 140 may act as a sensor, which receives acoustic signal 170. The received acoustic signal can be analyzed for monitoring purposes, such as to determine lubrication thickness or lubrication regimes in static and dynamic conditions. In some embodiments, the operating frequency of piezoelectric sensor 140 may be from 100 KHz to 400 KHz. In some embodiments, the operating frequency of piezoelectric sensor 140 may be from 100 KHz to 300 KHz. However, in other embodiments, the frequency produced by piezoelectric sensor 110 and detected by piezoelectric sensor 140 may be tuned to any suitable frequency. Notably, the frequency range utilized for active sensing is different from the frequency range for passive sensing, thereby allowing signals to be easily distinguished.

In a passive sensing mode, one or more of the piezoelectric transducers 110, 140 act as sensor(s) that detect acoustic signals. While the embodiment shown provides two piezoelectric sensors, in other embodiments, a single piezoelectric sensor or more than two sensors may be utilized in a passive sensing mode. In a passive sensing mode, acoustic signals are not produced by an external source. Movement of the components of an artificial joint may cause acoustic signals to be generated. For example, static deformation and vibrations due to abrasion and non-uniform loading of an artificial joint may create signals that sensitive piezoelectric transducers are able to detect. The received acoustic signals may be utilized for monitoring purposes, such as to detect impingement, stick-slip, surface damage or combinations thereof.

Experimental Example

The following examples are included to demonstrate particular aspects of the present disclosure. It should be appreciated by those of ordinary skill in the art that the methods described in the examples that follow merely represent illustrative embodiments of the disclosure. Those of ordinary skill in the art should, in light of the present disclosure, appreciate that many changes can be made in the specific embodiments described and still obtain a like or similar result without departing from the spirit and scope of the present disclosure.

State-of-the-Art: The Hip Joint Simulator

Wear resistance of surfaces is not an intrinsic material property, but depends on system variables such as operating conditions; type of counterface, environment, etc. A simulator can be described as a machine used to test a joint replacement under conditions approximating those occurring in the human body. Simulator tests, on the other hand, can be used to conduct accelerated protocols that replicate/ simulate particularly extreme conditions, thereby establishing the limits of performance for the material. Results from simulator testing can provide confirmation of the material's performance for a given geometric design under a variety of operating conditions. However, different simulator designs provide different wear results, which, in this sense, makes it impossible to compare wear results obtained using different simulators even when testing the same prostheses. This is because at the moment each one uses an internal protocol and does not follow ISO standards. Table 1 shows a list of the most well-known simulators available.

TABLE 2-1 specification of well-known simulators

| Author | Simulator | Station | Degree of Motion | Motion Simulated | Wear Rate | Position Head |
|---|---|---|---|---|---|---|
| Barbour (2000) | PROSIM Limited | 10 | 2-axis | BI-AX(±30°) | 42 ± 1 mm³/Mc | No anatomical |
| Smith (2001) | Mark II Durham | 5 | 2-axis | FE(+30°/−15°), IN-EX(±10°) | 50.32 ± 7.07 mm³/Mc | Anatomical |
| Nevelos (2001) | Leeds PA II | 6 | 2-axis | FE(+30°/−15°), IN-EX(±10°) | 0.11 ± 0.04 mm³/Mc | Anatomical |
| Bragdon et al. (2003) | AMTI | 12 | 3-axis | FE(±25°), AA(±9°), IN-EX(±20°) | 4.8 ± 1.1 mg/Mc | Anatomical |
| McKellop (2004) | EW08 MMED | 16 | 2-axis | FE(±22.5°) AA(±22.5°) | 0.4 mm³/Mc | No anatomical |
| Saikko (2005) | HUT-4 | 12 | 2-axis | FE(46°), AA(12°) | 8.2 mg/Mc | Anatomical |
| Clarke (2005) | SW | 12 | 2-axis | BI-AX(±23°) | 0.032 ± 0.028 mg/Mc | No anatomical |
| Affatato (2006) | SW | 12 | 2-axis | BI-AX(±23°) | 0.17 mg/Mc | No anatomical |

FE = flexion-extension, AA = abduction-adduction, IN-EX = internal-external rotation, Bi-AX = biaxial rocking, Mc = million cycles The hip prosthesis allows motion in all three planes: the sagittal, frontal, and transverse. Flexion, extension and hyperextension are all performed in the sagittal plane, with about 120 degrees of flexion, and 15 degrees of hyperextension. Extension of the hip occurs when the joint returns to anatomical position after being flexed. The neutral reference position of the hip joint is defined by the orientation of the skeleton in standing. Adduction and abduction occur in the frontal plane with a range-of-motion of approximately 45° of abduction and 25° of adduction from the neutral position. Internal and external rotation of the hip occurs in the transverse plane, with a range of motion of approximately 45° for each. Hip joint simulators are designed to replicate these positions. However, due to multiple factors including ROM of designed prosthesis, efficiency, etc., certain limitations are inevitable.

Hip Ambulatory Simulator Design and Experiment Setup

The design and setup of human hip ambulatory simulator as well as the data acquisition system are discussed herein. A hip motion simulator allowed implants to be tested for millions of cyclic loading under different loading and lubricant conditions. Additionally, high frequency signal sampling may be desired for advanced frequency domain analysis and digital signal processing. The disclosure presents in virtue of lambda ratio and coefficient of friction, the validation of the active sensing based lubricant thickness detection and lubrication regimes determination. By showing a strong correlation between our experimental results and the predicted estimation, the validity of the method can be confirmed. The disclosure shows the results from the static and dynamic testing of different thicknesses of lubrication, the lubrication regime identification, the detection of impingement and the surface damage testing performed on the hip simulator.

Overall Functionalities

In this disclosure, a simulator that mimicked ambulatory motion was designed to allow testing of the novel piezoelectric simulator under conditions similar to those provide an adjustable range of constant motion on the artificial hip joint installed under variable loading weights. The simulator was able to provide a FE motion from −30° to 30° with a fine adjustable maximum angle as well as controllable AA and IN-EX motions. In this disclosure, only the FE motion is conducted for mimicking ambulatory movements. The loading could be easily changed according to the need of simulating physiological conditions for people with varied weights. The motion of the simulator itself can be corrected, which will reduce the difference of each cycle to less than 1° in the IN-EX orientation. A continuous motion with such accuracy can be provided by the simulator for more than one million cycles, which is needed for testing.

Figure 6:
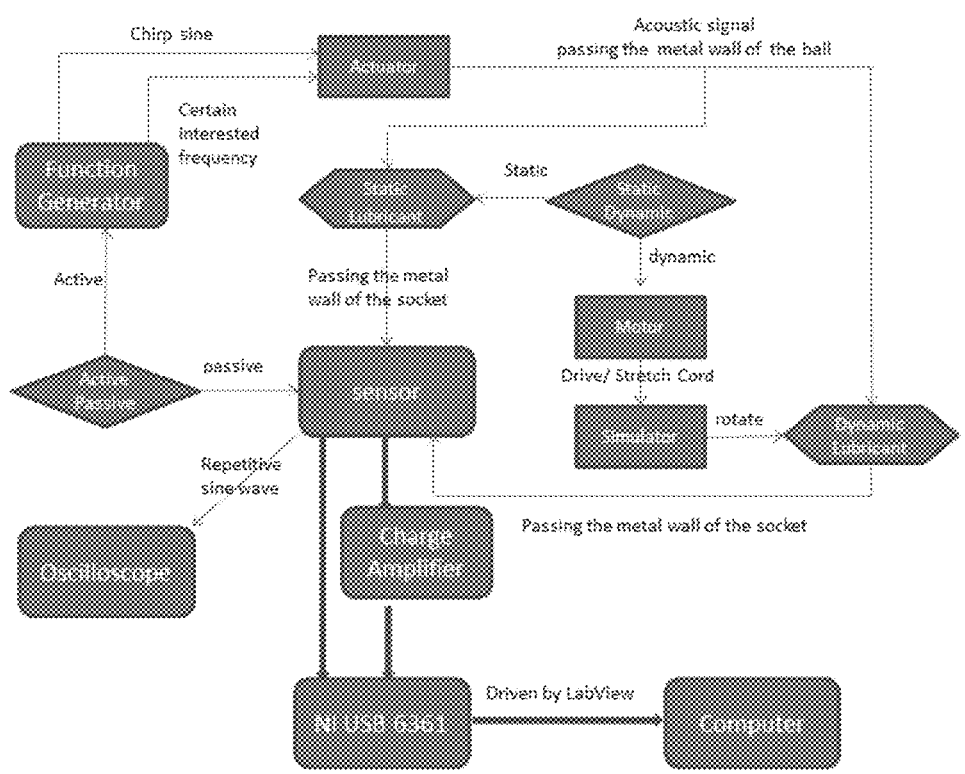
FIG. 6 is an illustrative embodiment of a block diagram of overall functionalities of a system for monitoring an artificial joint.

The loading system of the simulator is composed of a pendulum which rigidly connects to the artificial femoral ball and in this way, the loading is adjustable by switching the number of brick weights placed on the pendulum. The acetabulum socket is mounted on a Teflon holder which prevents the socket from tilting and moving. Meanwhile it also protects the socket from damage due to hard contact and overly large deformation. The driving system is comprised by a fixed screen wiper motor and a stretch cord. By adjusting the speed of the motor and the original elongation of the stretch cord, the range of motion can be adjusted to the maximal or ideal condition. Data recording involves multiple DAQ systems and oscilloscope. Also, an arbitrary function generator with upper frequency limit as high as 15 MHz is employed for generating designed signals. The overall functional block diagram is shown in FIG. 6.

Design of a Hip Motion Simulator

Figure 7A:
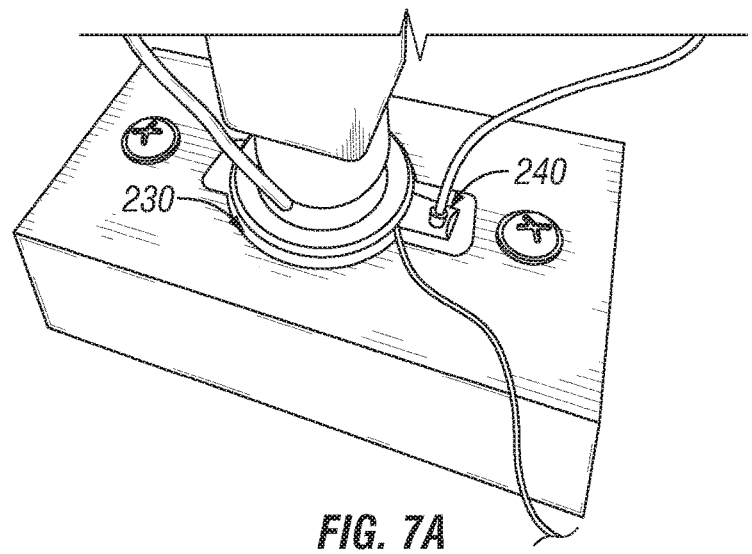
FIGS. 7A-7B are an illustrative embodiment of a hip ambulatory simulator.
Figure 7B:
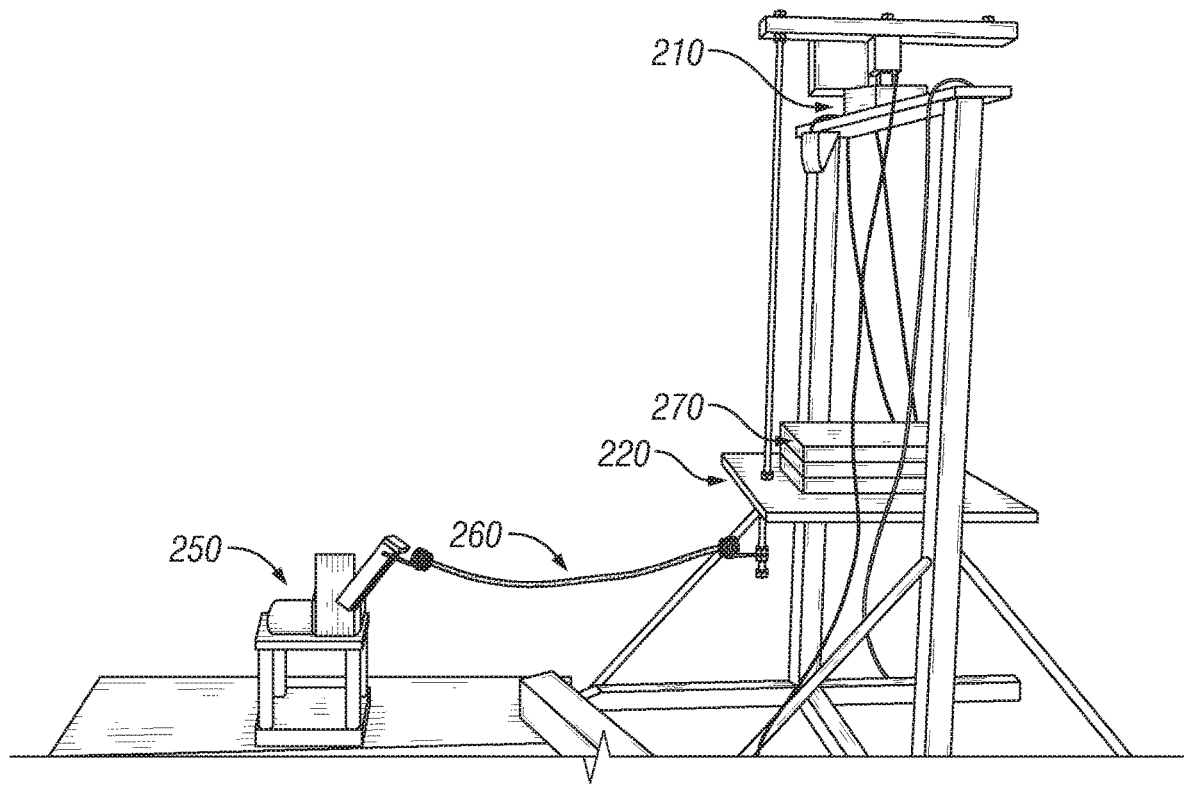

The mechanism of the whole structure could be simplified as a swing with an applied sine wave pulling force. The hip prosthesis is placed on the pivot so that periodic stress is applied on it once the motion of the swing is stable and fixed. Although the joint position is not anatomical, the design greatly takes the local loading profile and motion pattern of anatomical condition into consideration. As shown in FIGS. 7A-7B, the acoustic emission sensor 240 is mounted on the right side of edge of the acetabular cup 230.

The mechanism of the designed hip simulator is based on the kinetic principle of a pendulum. The contact area between the artificial femur ball and pelvic socket is approximately regarded as a pivot 210, neglecting the slight change of the contact area. The basic idea is to find the resonant frequency of the pendulum 220 and then excite the system with a motor 250, which is coupled to pendulum 220 via a cord 260, tuned to that same frequency. Weights 270 may be place on pendulum 220 to adjust the load. Since in this experiment the length of pendulum is changeable, the period of each testing cycle can be adjusted accordingly.

The total mass, $M_t$, loaded on the artificial hip joint is calculated by $$M_t = n \cdot m_1 + m_2 \quad (4\text{-}1)$$

where, $m_1$ is the mass of a weight; $m_2$ is mass of the load supporting, including the base support, the two connecting rigid helix bars and holder for the metal ball; n is the number of bricks loaded. Because both of the mass of the two bars and the torque of the ball holder are insignificance, it is neglected in the calculation. Therefore, here $m_2$ is the weight of the supporting plate.

Set the pivot as a datum mark, and define the length between each mass center and the pivot as $L_1$, $L_2$ and define the length from the pivot to the equivalent mass center of the whole system as $L_t$, then $$M_t L_t = n \cdot m_1 L_1 + m_2 L_2; \quad (4\text{-}2)$$

$$\text{so, } L_t = (7m_1 + m_2 L_2)/M_t; \quad (4\text{-}3)$$

The resonance frequency of a pendulum, is given approximately, for small displacements, by $$f = \frac{1}{2\pi}\sqrt{\frac{g}{L_t}}, \quad (4\text{-}4)$$

where g is the acceleration due to gravity (about 9.8 m/s$^2$)

Even though the actual movement of the simulator is with a large displacement and equation 4-4 is not accurately applied any more, the change of the motion, especially in the terms of period, due to the friction produced by the joint and other damping factors, is minor. Besides, the motor is adaptive to the change in its load. Therefore, to tune the swing in its natural frequency, equation 4-4 can be referred to.

Figures 8A, 8B:
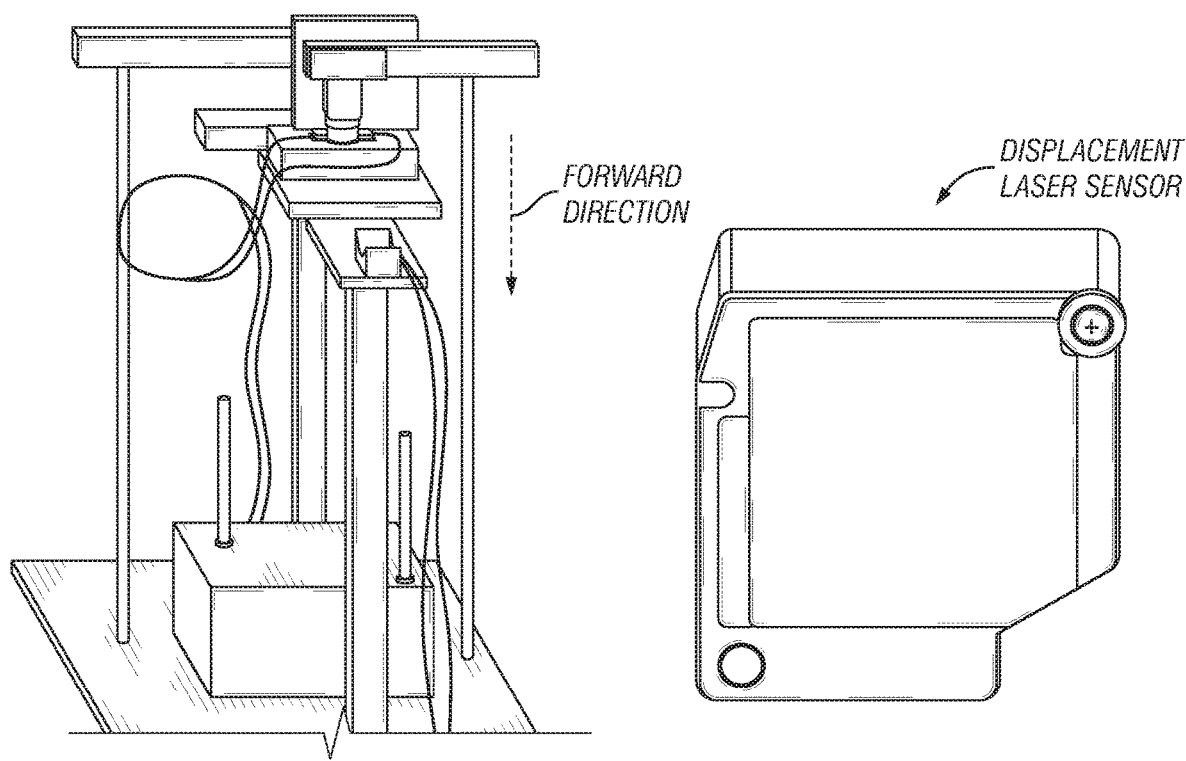
FIGS. 8A-8B are an illustrative embodiment of displacement laser sensor and forward moving direction.

The forward direction is defined as when the T shape bracket moves towards the laser sensor, as shown in FIGS. 8A-8B.

Simulation on the Artificial Hip Joint

A model of the simulator was made in the finite element software SAP2000. In the model, the articulation between the ball and the socket is simplified as point contact like a pivot with all the weight loaded. A rigid bar is connected to the pivot and is driven by a nonlinear spring. The other side of the spring is connected to another rigid bar whose center is fixed and can spin around its center.

Figure 9:
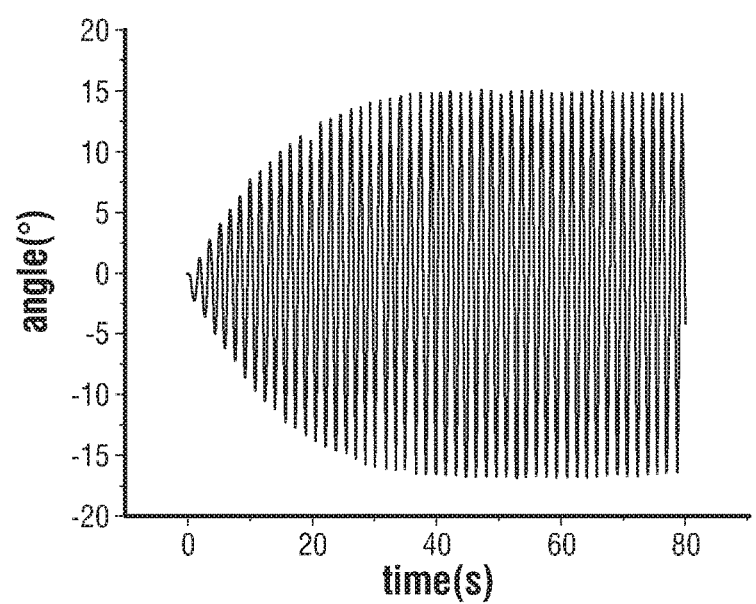
FIG. 9 is an illustration of a simulated motion of the simulator.

Taking one particular simulation as an example, the length of the driven bar is set at 15 cm; the mass is set at 200 lbs.; The equivalent length ($L_t$) is set at 65 cm. The elasticity modulus is considered as a nonlinear variable which is calculated and fitted by 10 sets of elongation and corresponding elasticity. The horizontal distance between the two fixed points is 90 cm. The simulated motion is shown in FIG. 9.

Figure 10:
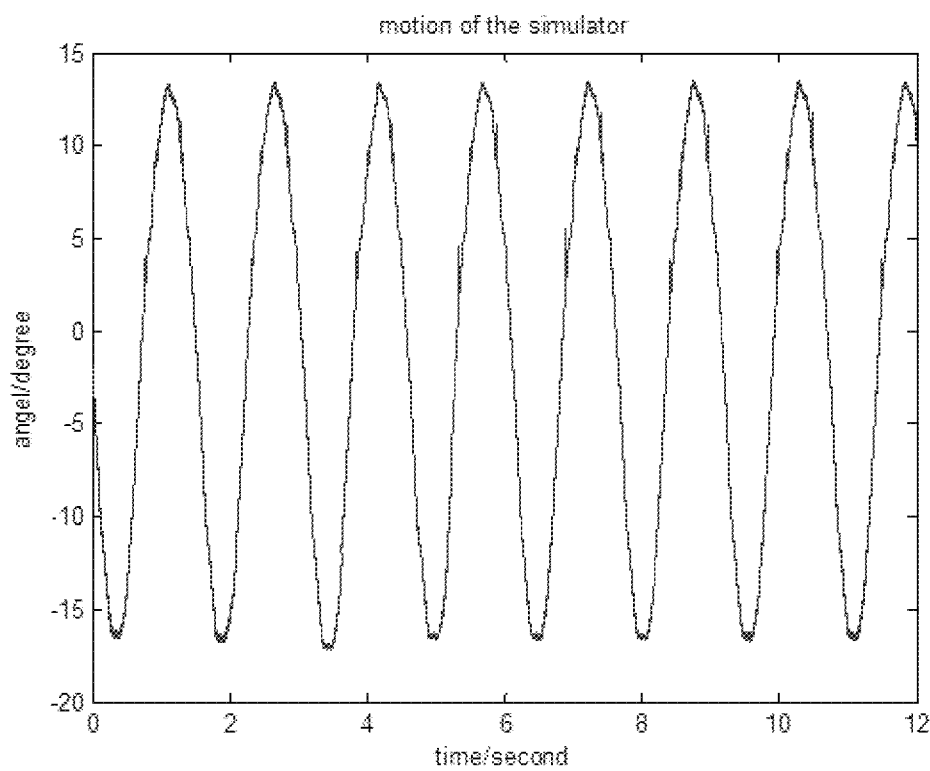
FIG. 10 is an illustration of the motion of a simulator captured by laser sensor.

After around 40 seconds, the motion tends to be stable. In the real application, such process can be greatly reduced by placing the motor further away from the pendulum. The period of one cycle is around 1.62 s. The maximal angle along the pulling direction is around 16.8° and the maximal angle of the other side is around 13.8°. Also, such angles are affected by the position of the motor. The period of the pendulum undergoing resonance is calculated to be 1.60 s. The measured period for the simulator by a displacement laser sensor is 1.553 s. The maximal angles are 16.6° and 13.2° respectively. As shown in FIG. 10, the data of the laser sensor is calibrated in terms of angles.

Data Acquisition System and LabView

The frequency bandwidth of interest is quite large. For static testing, a transmitted signal can be with a frequency as high as 15 MS/s. The change in the received signal with different lubricant conditions is still highly distinct. Thus, the requirement for the acquisition system is strict.

For picking up signals with a frequency higher than 300 KHz or for static testing, a Tektronix TDS 2024B Oscilloscope with a frequency limit up to 2 GS/s was used. It provides transient state recording and the data can also be downloaded to a flash drive through USB interface.

Since the frequency range of interest is from 100 KHz to 300 KHz, an NI USB 6361 board was employed. It has 16 channels simultaneous analog input at a sampling frequency of 2 MHz, which is high enough without much distortion. The board is driven by LabView. Alternative data acquisition systems like dSPACE and Data Translation were also employed in case the channels are not enough.

Figure 11:
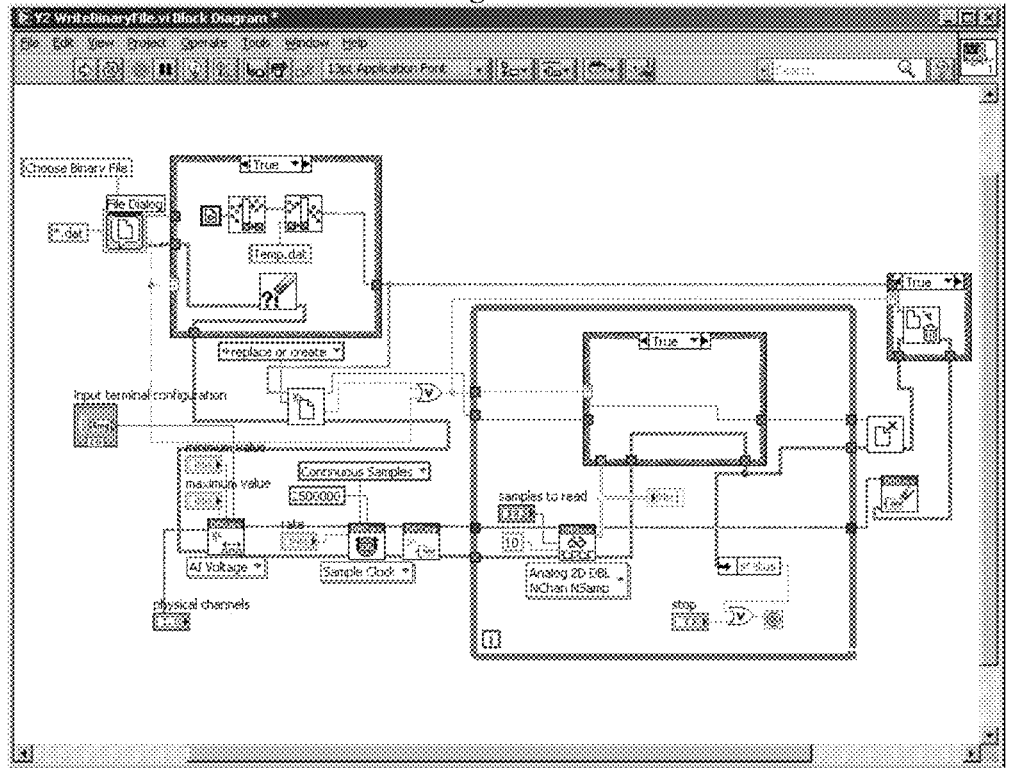
FIG. 11 is an illustrative embodiment of LabView program for data sampling.

Both the NI USB board and the Data Translation USB board need to be driven by LabView which is a graphical programming environment used for measurements, control systems, data analysis, etc. It is able to directly connect to any instrument or sensor with driver libraries installed. The software is mainly employed for access the sensor signal and analyze it. In FIG. 11, the program of sampling and recording the data with multiple channels is shown as an example. The program checks if there is a file name assigned. If yes, the computer starts to save the data in cache and once it meets the number of samples which is defined by customers, the data in cache will be written into memory and later hard drive in the same address where the file name corresponds to. If not, the computer will only read the data and display it without recording. The data can be saved in various formats, especially ".cvs", which can be imported into Matlab directly, orbinary formats like ".tms", which saves-more space and also enables faster response. In order to maximize the recording speed and veracity of the data, binary file without time variable and header is chosen for signal storage. The time data can be recovered later because the sampling frequency is known.

Validation of the Active Sensing Based Thickness and Regime of Lubrication Detection An active sensing approach using PZT transducers is employed to approximately predict the thickness of the lubricant and efficiently diagnose the regime of lubrication. However, to fully confirm the validity of such a method, an additional methodology with proven records needs to be implemented for comparison. Important indicators, such as Lambda Ratio and friction factors, were employed to identify and access different lubrication regimes. Confirmative data processing is utilized to find out the signature difference for all the regimes from the active sensing method.

Experimental Design and Setup

The experiment was designed to achieve all the regimes of lubrication on the edge of the hip resurfacing joints, a region mostly inclined for the breakdown of the lubricant to occur.

Experiment Setup

Figure 12A:
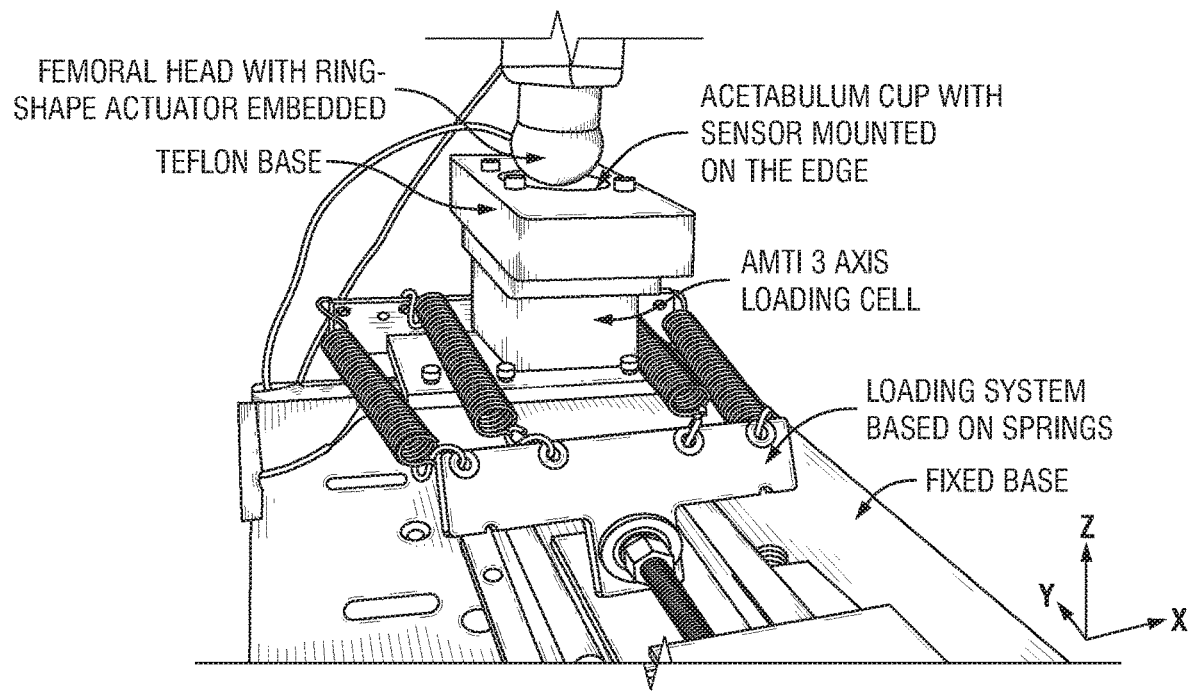
FIGS. 12A-12B are an illustrative embodiment of an experiment setup.
Figure 12B:
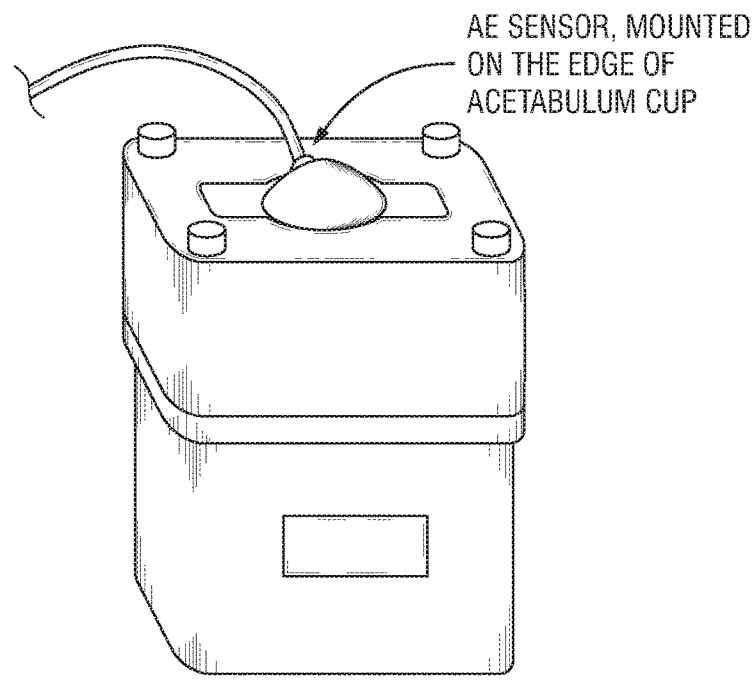

In FIGS. 12A-12B, a complete experimental setup is shown. The position of the prosthesis was chosen not to be anatomical considering the simplicity of implementation and the ball and socket was placed in a vertically aligned condition. To protect the socket from damage and movement, a Teflon holder was fixed together with the acetabular cup on an AMTI 3-axis load cell. The load cell was fixed on another holder rigidly linked with a one dimension slide which is clamped on an MTS 858 Mini Bionix II machine. The feedback controlled MTS machine with high speed communication provides highly precise vertical specimen loading and programmable axial rotation. An edge loading device with four springs was integrated on the slide by a long bolt. The bolt went through the hole with matched threads on the slide on one end and was fixed on the holder of the loading cell on the other end. By cranking the bolt, the springs was prolonged and thus a side loading was provided on the holder and the loading eventually acted on the edge of the ball and the socket. The edge loading and the axial toque of the ball and socket can be detected by the three axis loading cell and the data of each run was recorded in a computer. The spring based loading system greatly reduced the decentralization of the ball and socket induced pressure and torque by dissipating the energy in the deformation of the springs as the ball rotated.

On the edge region of the external part of the socket, a PZT based acoustic emission sensor was mounted. The sensor was connected to a charge amplifier which was then linked with the DAQ system for data collection. The PZT actuator, driven by an arbitrary function generator, was placed inside the ball. Active sensing was performed as the simulator operated.

Loading Profile

The experiment was performed under a wide range of loading in order to access all the lubrication regimes and a variety of lubricant thicknesses. A vertical load of 5.6 lbs. of was first added to stabilize the relative position of the acetabular and femoral components. Then, side loads were added ranging from 50 lbs. to 350 lbs. in 50 lbs. increments. Such loading could be precisely achieved by adjusting the bolt and reaching the calculated voltage shown from the data of the loading cell. Then, the edge loading meant that the load along the y direction varied from 0 lbs. to 350 lbs. To calculate the friction factor, the torque along the z direction was also recorded.

For each side loading, a set of rotations of ±40° (forward 40° to reverse) 40° along the z direction was performed at both 0.5 and 1 Hz, videlicet 1.396 and 2.793 rad/s. In each run, the simulator provides a successive 10 cycles of rotation. The torque in the x and y direction was kept zero or a constant. So was the force in x and z directions.

Parameters of the Lubricant and Prosthesis

In the experiment, 25%, 75% and 100% in volume of fetal bovine serum was used as the lubricant. Distilled water was used as a dilution solution. The protein concentration of the bovine serum was 62.43 g/L and the viscosity of the bovine serum was 0.001, 0.0025, 0.005 Pa s.

The clearance of the prosthesis was 50 μm. The equivalent elastic modulus of Co—Cr—Mo to Co—Cr—Mo was 231 GPa. Roughness values were 0.02 and 0.01 micrometers for Ra and Rc respectively.

Estimation of Lubricant Thickness and Lubrication Regimes

Figure 13:
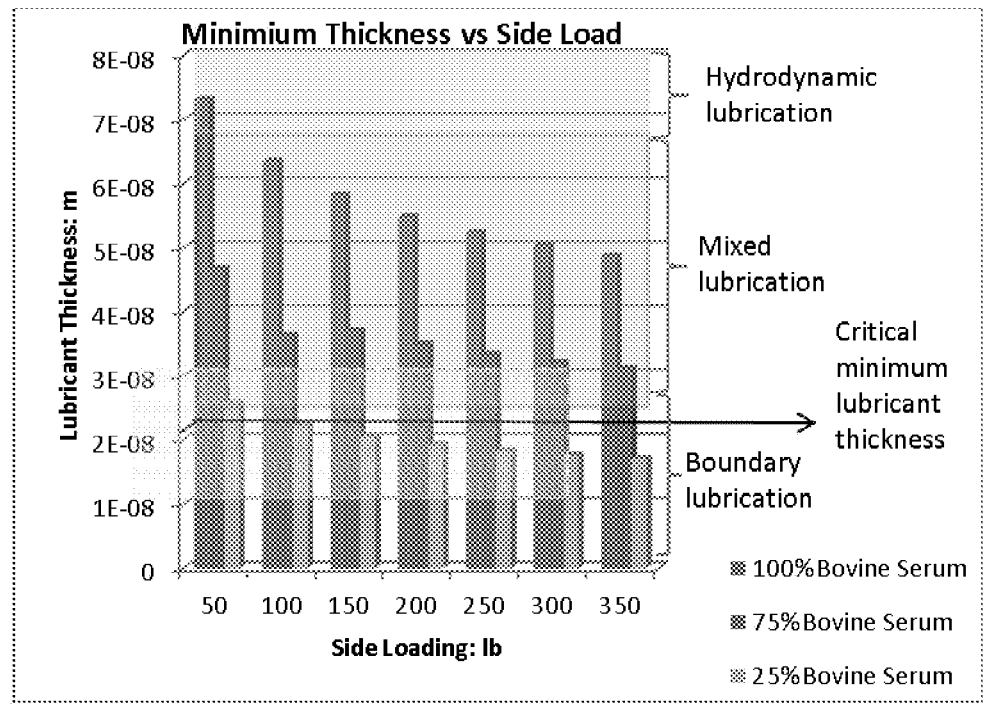
FIG. 13 illustrates estimated minimum film thicknesses.
Figure 14:
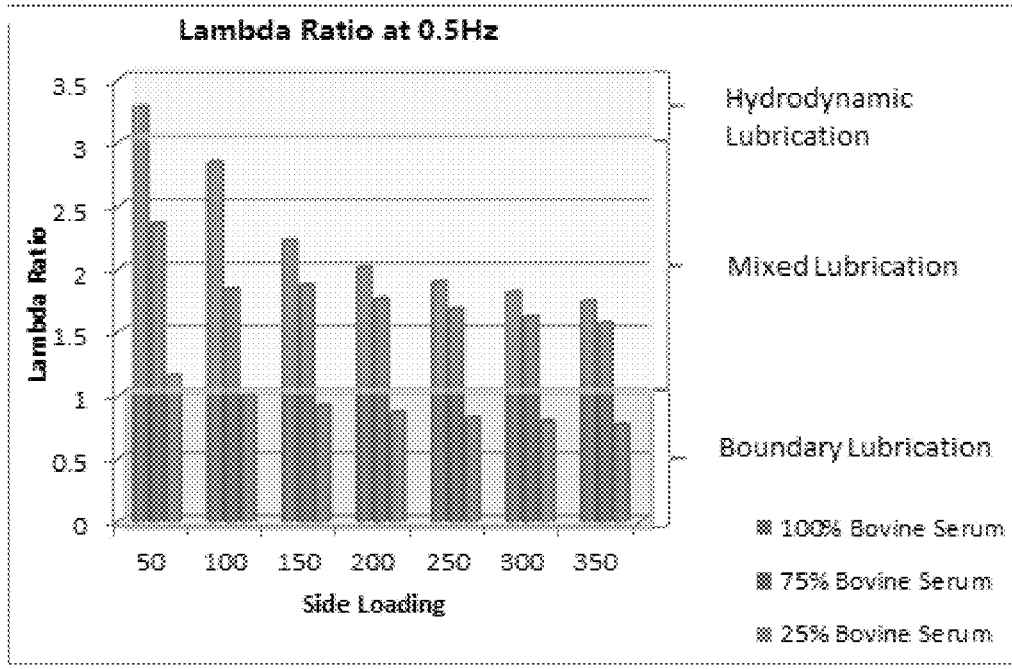
FIG. 14 illustrates estimated lambda ratios.

The minimum lubricant thickness, referred to in equation 2-1, was estimated and the lambda ratio was then calculated. As shown in FIGS. 13 and 14, the minimum lubricant thickness and corresponding lambda ratio were calculated for each loading profile.

When the thickness of the lubricant is reduced to 20 nm or even less, the running-in wear and the steady state wear increased dramatically. Thus, 20 nm is considered a critical value of minimum lubricant thickness. As shown in FIG. 13, in the experiment with 25% bovine serum, the lubricant thickness started to approach the critical thickness when the loading was larger than 150 lb. It is also indicated in FIG. 14, under the same loading profile, boundary lubrication regimes were present. For the 75% bovine serum, the lambda ratios under the loading from 50 lb to 350 lb were all larger than 1 and less than 3, which indicated the prosthesis was operating in mixed lubrication all the time with 75% bovine serum as the loading increase from 50 lb. to 350 lb. For the 100% bovine serum, the lambda ratio was more than 3 under the loading of 50 lb, which meant the hydrodynamic lubrication was obtained with the loading profile. All the rest of the lambda ratios with 100% bovine serum were less than 3. In other words, mixed lubrication was present. In conclusion, all the three key lubrication regimes were achieved in the experiment. The boundary between film fluid lubrication and mixed lubrication was achieved around the condition between 50 lb and 100 lb side loading at 0.5 Hz with 100% bovine serum. The dividing line of mixed and boundary lubrication was around 100 lb. at 0.5 Hz with 25% bovine serum.

Active Sensing for Lubricant Regime Determination

Figure 15:
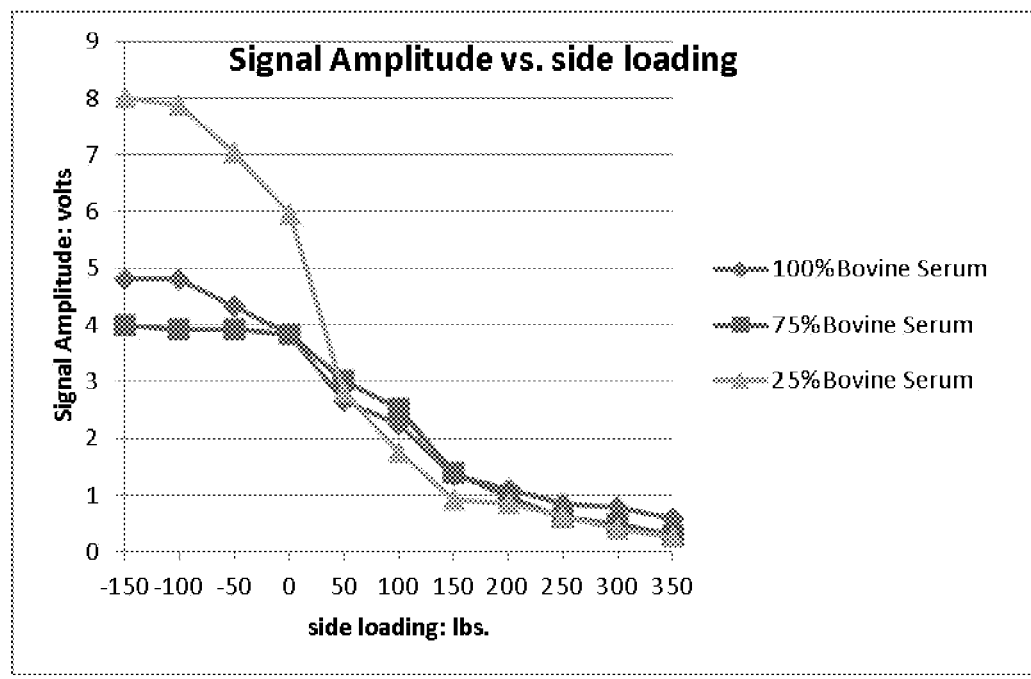
FIG. 15 illustrates signal amplitude v. side loading.

Signature Frequency Selection and Static Thickness Testing:

In this experiment, the clearance between the socket and the ball was filled with lubricant and any excess fluid was allowed to escape. The change in the thickness of lubricant was then observed using the transducer system during the application of side loading to the acetabular socket. As the loading was increased, the thickness of lubricant was gradually decreased due to the pressure squeezing the lubricant out of the approaching surfaces. The sensitivity of the change in the thickness of lubricant towards acoustic and ultrasonic signal with different frequencies was studied. An interested frequency lies from 100 KHz to 300 KHz, which was also the operating frequency of the acoustic emission sensor. With the help of an oscilloscope, the transmitted signal was recorded precisely with different activating sine waves when the side loading varying from −150 lb lbs. to 350 lbs. at a 50 lbs. interval. The negative sign meant the side loading was added in the opposite direction (−y direction in FIG. 12A). Thus, a negative loading provided more clearance or lubricant thickness. After comparing the data, the signal with 260 KHz was chosen for demonstrating the correlation between the amplitude of the sensor data and the side loading, because the transmitted signal at this frequency showed the clearest variation tendency in the amplitude as the side loading increased. Even though there was a slight difference in the magnitude of the transmitted signal with different frequencies, the tendency of how the signal changes as the thickness of lubricant decreased stayed the same. In FIG. 15, the correlation between the magnitude of signal and the change of loading is shown. The magnitude of the signal when there is no lubricant applied was 0.02 to 0.03 volts.

Figure 16:
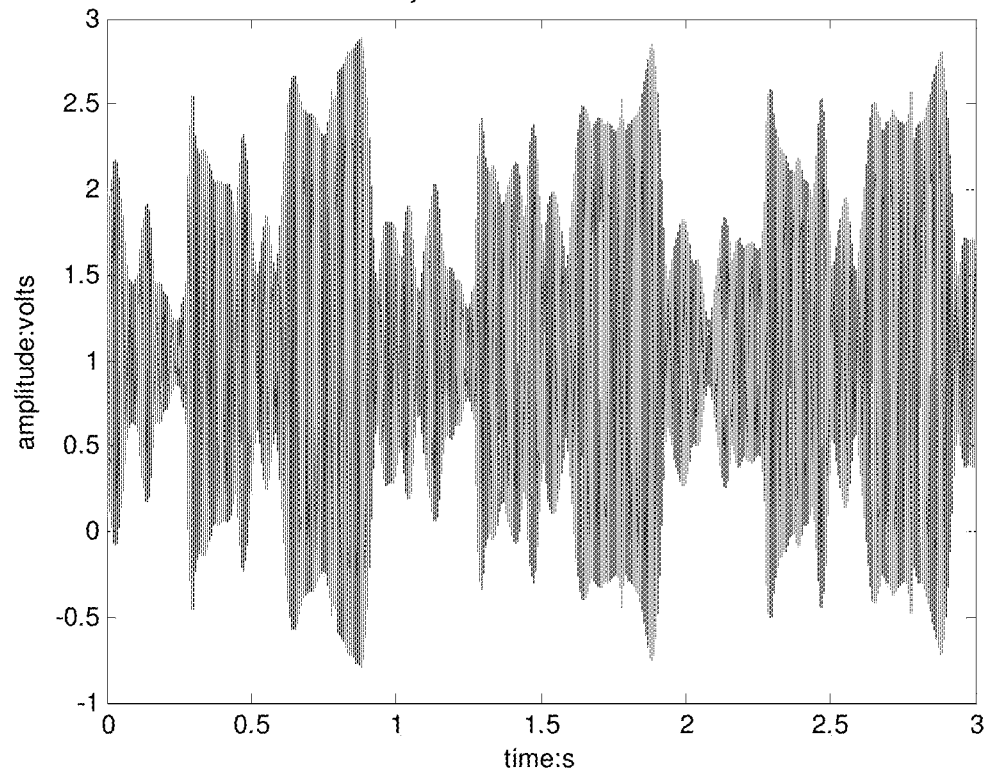
FIG. 16 illustrates a dynamic testing example.

Dynamic Lubrication Testing:

In the dynamic testing, from the data detected by the load cell, lambda ratio could be easily calculated as stated before. Thus, the data from two different methods: the estimation method using lambda ratio and the active sensing method could be compared to validate the latter method. For the reason of the micro decentralization between the femoral head and acetabular cup of the prosthesis and the lubricant flow, the thickness of the lubricant was changing in real time. The ultrasonic signal, which can be easily captured by PZTs, is very sensitive to such change. FIG. 16 shows a typical dynamic testing result for 3 cycles running at 100 lbs., 1 Hz with the 100% bovine serum as the lubricant. The repetitiveness of the signal can be clearly seen.

Determination of Lubrication Regimes Using Active Sensing:

According to FIG. 13, the transition between hydrodynamic and mixed lubrication lays between 50 lb. and 100 lb. at 0.5 Hz with 100% bovine serum. Thus, the data based on active sensing was also compared at these two loading profiles, as shown in FIG. 16.

For the data obtained at 50 lb. side loading, the smallest peak-to-peak amplitude of the signal was around 1.32 volts about ⅓ of the maximum peak-to-peak amplitude, which indicates the volume of lubricant is still favorable even when the peak-to-peak amplitude reached a relatively small value. The contour of the signal was relatively smooth. On the other hand, the smallest peak-to-peak value under the loading of 100 lbs. was 0.23 Volts at 1.2 s which was lower than the value of data at 350 lbs from static measurements. Such amplitude was about 1/20 of the maximum amplitude, which indicated a sudden drop of lubricant thickness. The results were consistent with the features of the two lubrication regimes. For the hydrodynamic lubrication, the change in lubricant thickness was only caused by the lubricant's hydrodynamic action. At a rotational speed as low as 0.5 Hz, the lubricant thickness was unlikely to have experienced obvious changes. However, when it comes to the mixed lubrication, asperities from two surfaces occasionally get in contact with each other and the lubricant thickness was reduced to that of boundary film, which was a thin layer of protein attached on the metallic surfaces. At any other time, the amplitude was generally at a high level which indicated the condition was still near fluid film lubrication.

Figure 17A:
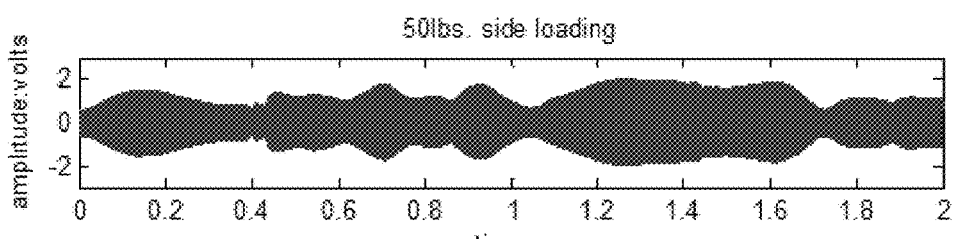
Figure 17B:
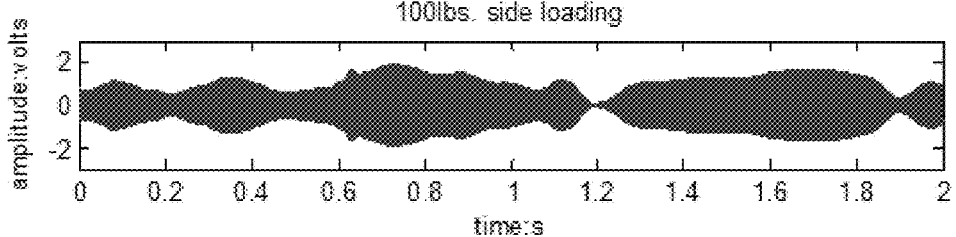
Figure 17C:
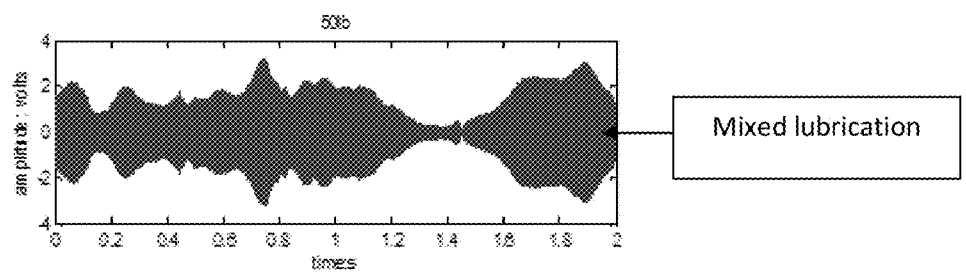
Figure 17D:
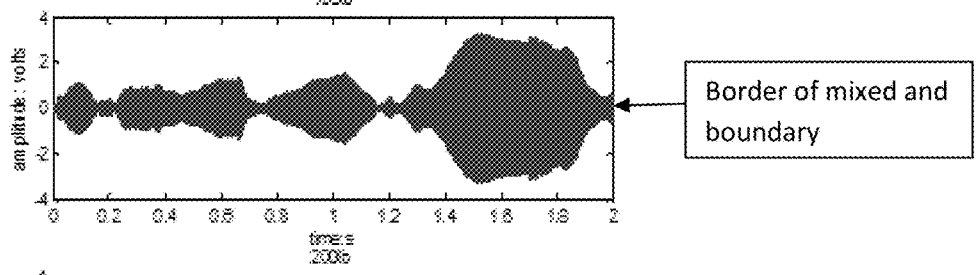
Figure 17E:
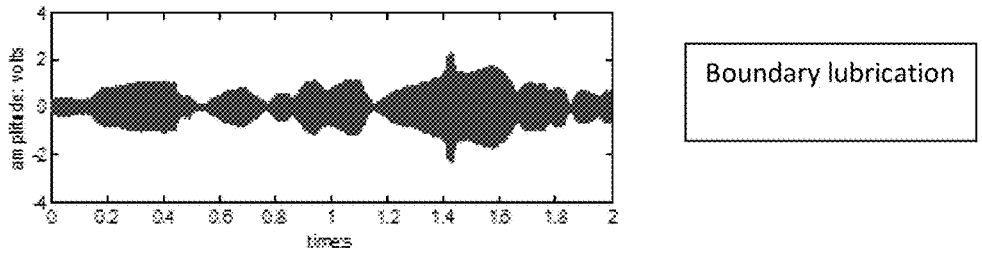

As the loading increased, the thickness of the lubricant became thinner and thinner. At 0.5 Hz, 100 lb loading with 25% bovine serum, the regime switched to boundary lubrication from mixed lubrication. As shown in FIGS. 17A-17H, the sensor signals among different lubrication regimes are compared. FIGS. 17A-17B illustrate the difference between hydrodynamic (FIG. 17A) and mixed lubrication (FIG. 17B). FIGS. 17C-17H further illustrate different lubrication regimes and their relationship with the Lambda ratio.

The data obtained at 50 lb. shares similar features with the mixed lubrication signal in FIG. 16. The overall amplitude is relatively high and occasionally encounters a sudden drop. However, the minimum peak-to-peak amplitude is about 0.1 volts, larger than the amplitude of direct metal contact signal. It is considered as a contact between asperities with an attached boundary layer. On the contrary, at 100 lb, the minimum amplitude of the data started to reach 0.03 volts, which strongly indicates a breakdown of the lubrication. As the load increased further, such breakdown occurs more frequently. In addition, the overall amplitude keeps decreasing quickly in boundary lubrication regime as the load increases.

Additionally, within one cycle of testing, the thickness of the lubricant varies due to the imperfect smoothness of the articulating surfaces. The amplitude of the sensor data also varied according to the changes in lubrication thickness as shown in FIG. 14, 19. Thus by checking the distribution of measured amplitude with regards to different loading, an approximate distribution of film thickness in different regimes can be looked up. For example, for the data corresponding to 350 lb. side loading, 50% of the amplitude distributes in the range of 0.03 to 0.1 volts. For the data corresponding to 50 lb. side loading, 53% of the amplitude distributes in the range of 2.5217 to 3.2132 volts. In FIG. 18, the distribution of sensor data's amplitude is compared among 50 lb., 100 lb., and 350 lb. with 25% bovine serum. The prosthesis operates in boundary lubrication with 25% bovine serum and 350 lb. side loading while it operates in mixed lubrication with 25% bovine serum and 50 lb. side loading, as shown in FIG. 13.

As shown in FIG. 18, the signal amplitude obtained at 350 lb. side loading stayed mostly within 0.1 volts to 0.4 volts. This is consistent to the feature of boundary lubrication, where the load is dominantly supported by a thin layer boundary film. No peak-to-peak value is larger than 0.7 volts. On the other hand, the signal amplitude with a loading of 50 lb. stayed mainly around 3 volts. No peak-to-peak value reached past 0.03 volts.

To figure out the correlation between the transmitted signal and lubricant regime, a parameter describing the average amplitude of one cycle's signal, is defined as the average of maximum peak-to-peak amplitude (AMPA) of one cycle's signal. The reason to choose the average maximum value instead of the average mean value is due to the limitation of the DAQ system, since the sampling frequency applied is only around four times of the activation signal frequency. Thus, a peak value is likely to get lost, which can lead to the distortion of the signal. A segment of 0.1 ms (running at 0.5 Hz) which only covers 1/20000 of a cycle is chosen to be the maximum unit representing maximal peak-to-peak amplitude to calculate AMPA. In other words, the thickness of lubricant is unlikely to have great change in such a short duration of time. Therefore, the average maximal peak-to-peak amplitude is approximately equal to the true average mean peak-to-peak value. Since the latter one in real situations is hard to obtain, AMPA is then defined as the average maximal peak-to-peak value.

Figure 19:
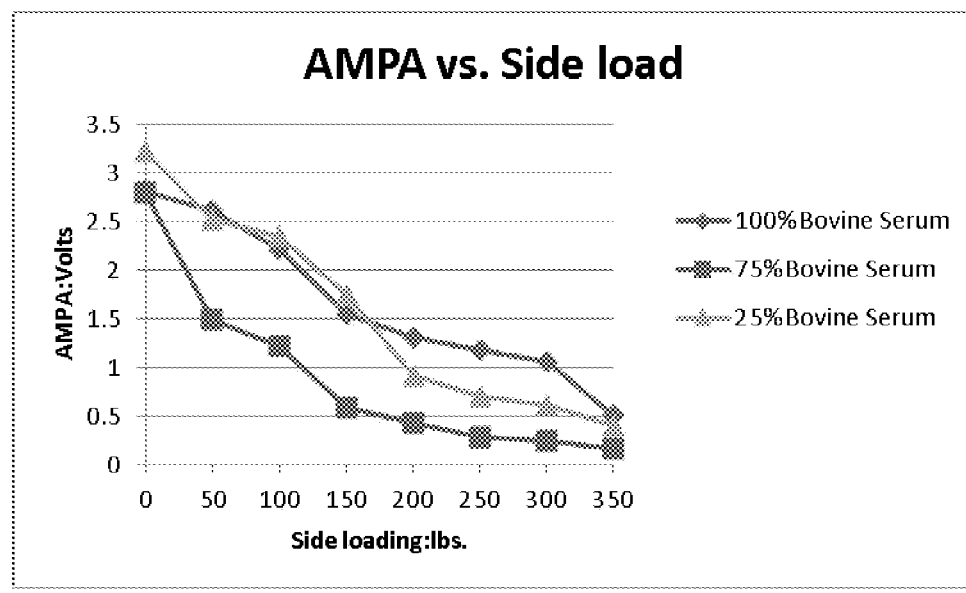
FIG. 19 illustrates AMPA v. side loading (running speed: 0.5 Hz)

As shown in FIG. 19, the AMPA of all the three lubricant decreases as the loading increases. It has been found that the minimum lubricant thickness and the average lubricant thickness share the same tendencies to the change of loading, retraining speed and viscosity. Also, the lubricant minimum thickness is in direct proportion to the corresponding lambda ratio according to equation 2-4. Thus, the method of detecting lubrication regimes is then given with the help of the waveform of the transmitted signal in dynamic testing and the comparison with AMPA. By identifying the feature shown in FIG. 16 and FIGS. 17A-17H, the lubrication regime can be determined immediately. The AMPA can be used to confirm the lubrication determination. Once the two boundaries of the lubrication regimes are determined, the range of corresponding AMPA of each regime is fixed. For example, as shown in FIGS. 17A-17H and 19, the data with a side loading of 100 lb was determined as the border between mixed and boundary lubrication. Thus, if a set of data has an AMPA smaller than the AMPA of the signal with 100 lb side loading, then the prosthesis can be confirmed to operate under boundary lubrication in the loading profile corresponding to such set of data.

This demonstrates the validity of the active sensing method for detecting lubrication regimes. The determination of the lubrication regimes based on the active sensing method is consistent with that based on lambda ratio estimation. The results show for the 100% bovine serum under the loading of 50 lb, the prosthesis works in hydrodynamic lubrication; for 75% bovine serum, the prosthesis works in mixed lubrication under the loading from 50 lb to 350 lb and for 25% bovine serum, the prosthesis starts to work in boundary lubrication once the loading is larger than 100 lb.

Hip Ambulatory Simulator Testing Results

Stick-Slip Detection:

In practical dynamic applications, it is difficult to use microscale techniques to detect the regime of lubrication. After surgery, it is hard to calculate the coefficient of friction or the lambda ratio, due to the difficulties of accessing some key factors. Therefore, it is important to develop a method of identifying the current regime of lubrication and help the physicians to diagnose the health state of implants so that a timely measure could be taken in order to prolong the life of the implants. A method of picking up signature phenomenon and unique features of boundary lubrication that has been developed, with low cost and fast response, as discussed below.

Typically, the kinetic friction coefficient between two surfaces is smaller than the static friction coefficient. Once a considerable force is applied, the reduction of the friction from static to kinetic can cause a sudden leap in the velocity of the movement. Such spontaneous jerking motion while two surfaces start to slide is called stick-slip phenomenon.

In boundary lubrication, the loading is mainly carried by the metal-to-metal contacting area or asperities. Unlike well lubricated articulation with insignificant stick-slip phenomenon, in boundary lubrication such phenomenon is predominant.

Figure 20:
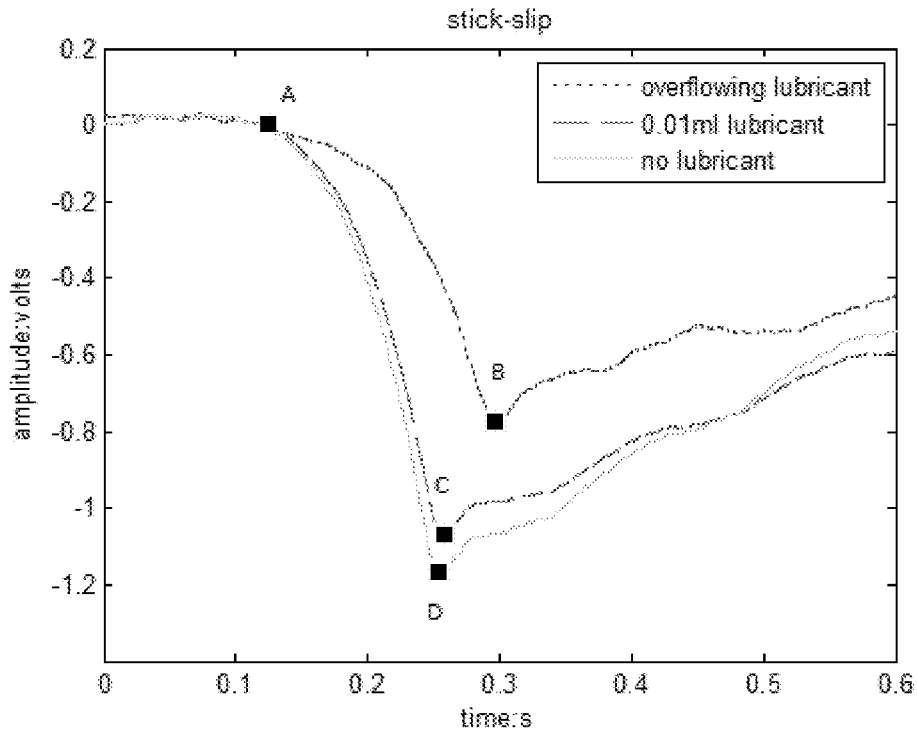
FIG. 20 illustrates signals during stick-slips in boundary lubrication.

The experiment compares the following three conditions: overflowing lubrication (when lubrication starts to overflow the cup), 0.01 ml lubrication, and no lubricant. In this experiment, 100% bovine serum was used as lubricant. A 20 lb. weight was added each time. Thus, for 7 weights, the total mass on the simulator was 200 pounds. The motor was adjusted to a slightly less than 270° which also tilted the pendulum to a small angle, and the motor was adjusted to the same angle each time. Also, for each experiment, the tilted angle of the pendulum was adjusted to the same. When the motor was started, the pendulum started to fall and the data was recorded. Among the three conditions (overflowing vs. 0.01 mL lubrication), the signal resembled each other until the sixth weight is added. There was a major difference at the time when the joint started to move. FIG. 20 shows the sensor signal between two different conditions when the load was 200 lbs. In particular, A (x: 0.1254, y: −0.005409), B (x: 0.2991, y: −0.7827), C (x: 0.2596, y: −1.073), and D (x: 0.2562, y: −1.233) in FIG. 20.

From the coordinates in the plot, at around 0.1254 s, the ball's surface and the cup's surface begin to have relative motion. The dot line, dash line and solid line hit the first valley at 0.2991 s, 0.2596 s and 0.2562 s, respectively. In other words, it takes 0.1737 s, 0.1342 s and 0.1308 s for the each curve to drop to the valley. The dash line and solid line dropped much faster than the blue line. However, the time difference between the red and green is minor. Such time difference was verified by the data collected by a laser sensor, which indicated the time of the pendulum dropping from the beginning point to the lowest point. The time spans from the beginning point to the turning point are 0.173 s, 0.134 s and 0.131 s. Thus, the time difference between three curves in FIG. 20 might be caused by a leap in the velocity of the case with 0.01 ml and no lubricant when the pendulum begins to move.

Figure 21:
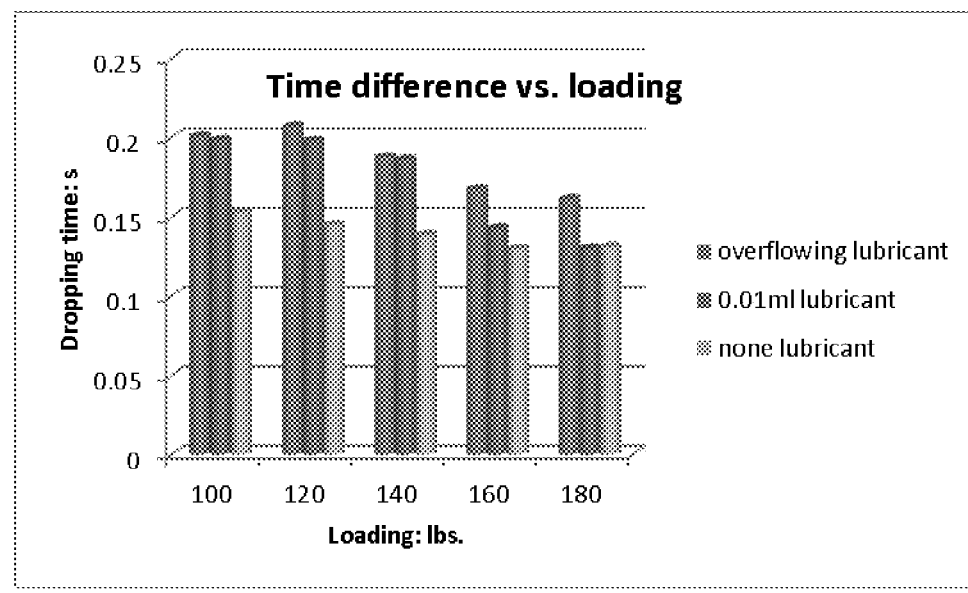
FIG. 21 illustrates time difference vs. total mass.

FIG. 21 shows the difference in the time needed to go from point A to the other points (B, C or D), which represents different loading conditions. However, the initial angle does not stay the same as the weight increases, thus it is not meaningful to compare the time span between different loadings. However, clearly, as the loading decreases, the time difference between overflowing and 0.01 ml lubricant become very small. But when the load is more than 160 lbs., there is considerable difference between overflowing and 0.01 ml lubricant. On the contrary, the difference between 0.01 ml and no lubricant reduces. This might also indicate for 0.01 ml 100% bovine serum with a loading of 160 lb. loading is approximately the boundary between mixed and boundary lubrication. However, such deduction is not proven by other existing methods.

Static Testing of Lubricant Thickness:

In the condition that the surface roughness of the joints is known, the easiest way to determine the regime of the lubrication is to measure the thickness of the lubrication, which could actually be calculated by certain dimensions of the prosthesis. However, this is assumed under the circumstance that the prosthesis is working properly. When the lubricant degrades and less lubricant remains between the two surfaces, the lambda ratio cannot be calculated using the above method. It is imperative to develop a feasible method to predict the thickness of the lubricant in real time post-implantation. In this section, an active sensing strategy was used to approximately predict the thickness of the lubricant. Acoustic or ultrasonic waves attenuate greatly as they traveled through air, lubricant and metal, and especially through multiple layers of materials. In virtue of the ambulatory simulator, another testing was performed to test the connections between volume of the lubricant and the amplitude of the transmitted signal.

In this experiment, a linear sine chirp signal was applied to discover how the attenuation of the acoustic signal is affected by its frequency. The chirp signal is given by $$f(t)=f_o+kt \text{ and} \quad (5\text{-}1)$$

$$x(t)=A \sin [2\pi(f_\perp 0+k/2t)t], \quad (5\text{-}2)$$

where A is the amplitude of the chirp signal, $f_o$ is the starting frequency, t is current time and k is the speed of the increase of the frequency.

Preliminary tests were performed and indicated that the major change of amplitude between no lubricant and with lubricant lie in the range between 100 KHz to 300 KHz. Additionally, since the chirp signal provides the same amplitude of sine components with different frequency, the amplitude of the signal picked up by the sensor stands for the energy itself. Thus, a chirp signal, with a starting frequency at 100 KHz and a stopping frequency at 300 KHz, was generated by the arbitrary function generator and the signal was sent into the actuator. For certain frequencies, the difference of the signal picked up by the PZT sensor is quite significant. The signal behavior also changes when the lubricant varies.

Figure 22:
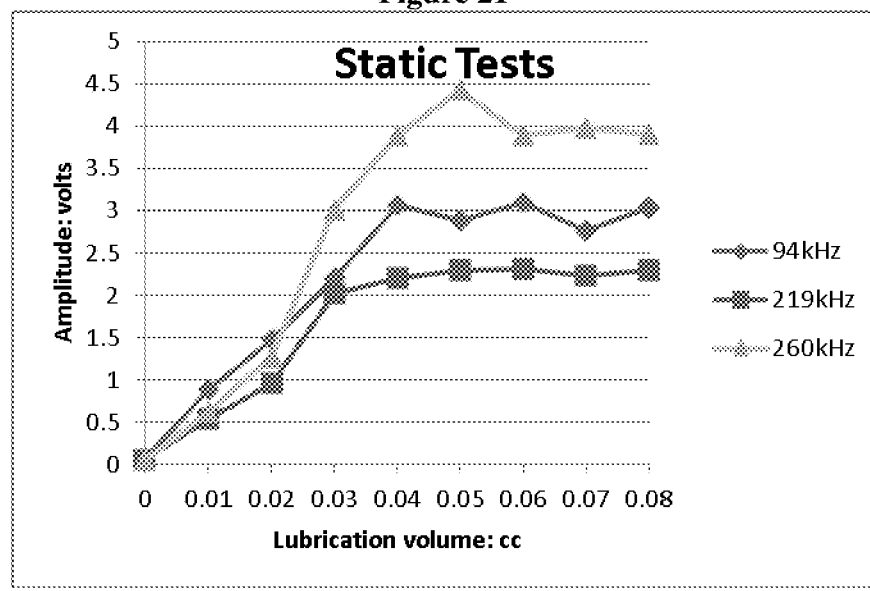
FIG. 22 illustrates static testing results.

Due to the transience of the stay in each frequency within the range, a close survey was needed. In FIG. 22, the static testing was performed under 100 lb. loading with 100% bovine serum.

Clearly, the amplitude of the signal rapidly increases at first and after a breaking point, it tends to stay the same albeit with small oscillations. The result does not contradict the validation in the Hip Ambulatory Simulator Design and Experiment Setup section. It is notable that in this case, despite the increasing volume of lubricant, the maximum volume of lubricant staying between the two surfaces is limited once the weight on the simulator is fixed.

Dynamic Testing of Lubricant Conditions:

Dynamic testing was carried out at the frequency of 260 KHz, which is the frequency most sensitive to the changes of lubrication conditions. Two sets of experiments were performed. First, the quantity of the lubricant applied was changed. Second, the amount of lubrication overflowed the test specimen while the loading weight was increased from 40 lbs. to 200 lbs.

Figure 23:
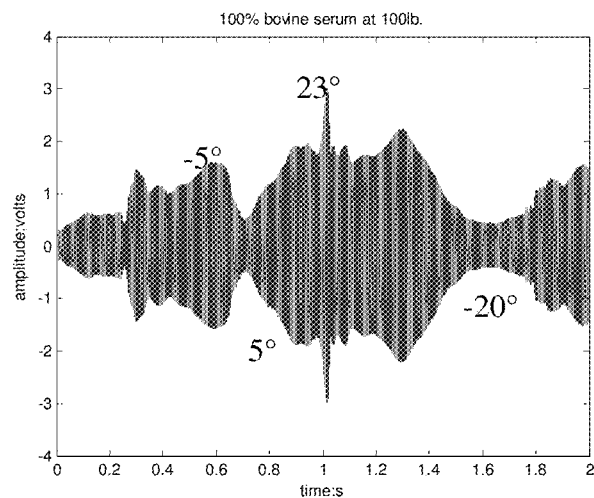
FIG. 23 illustrates hydrodynamic lubrication.

The lubricant generally operated under hydrodynamic lubrication, as shown in FIG. 23. The wave shape is consistent with the signals obtained from a hydrodynamic regime, which was discussed in the Determination of Lubrication Regimes Using Active Sensing section. The forward and reverse direction is referred to FIGS. 8A-8B. The angle is detected by the laser sensor. At −20°, the T shape bracelet was at the largest distance from the laser sensor; the pendulum moved mostly towards right; the stretch cord was stretched to the maximum length. The loading was then mainly applied on the side of acetabular cup which the acoustic emission (AE) sensor is mounted to. Thus, at this time, the lubricant between the femoral head and acetabular socket had the minimum average thickness if the hydrodynamic motion of the fluid is neglected. On the other hand, as the pendulum moved to the other side, the reverse loading increased the clearance between the femoral head and acetabular cup on the sensor's side. As the lubricant filled in the clearance, the thickness of lubricant became larger. That is the reason the signal amplitude is generally larger around 23°. According to observation, at 23°, the pendulum was at the highest position, and the direction of motion started to change. However, probably due to the inertia of the fluid, the lubricant continued moving up briefly before dropping back down. Such a motion created a peak in sensor data. Also, the signal had another drop at around 5°. It could be caused by the motion of the lubricant due to the beginning of change in the direction of acceleration. The hydrodynamic motion of the lubricant needs to be investigated for a more precise explanation.

Figure 24:
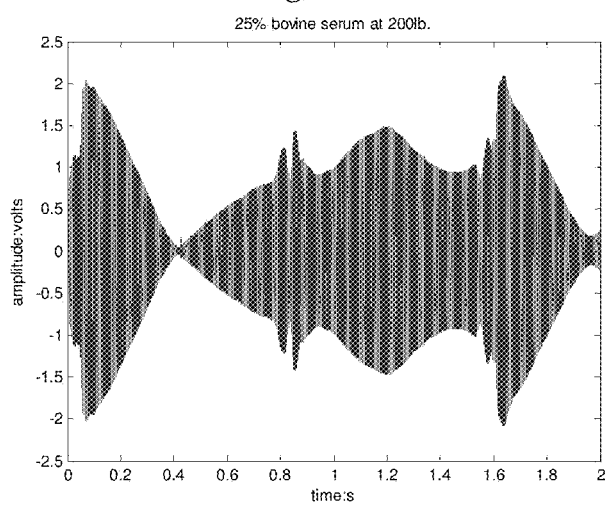
FIG. 24 illustrates breakdown of the lubricant.

As the loading continued to increase and the viscosity continued to decrease, the breakdown of lubrication occurred at 200 lbs. with 25% bovine serum, as shown in FIG. 24, with minimum peak-to-peak value of 0.056 volts. The clear dropping tendency of the amplitude of the signal between 0.1 s and 0.4 s shows the process in which the lubricant was squeezed out or was squeezed to the other side.

Detection of Impingement:

An advantage of PZT sensor is that it is very sensitive to collision signals. In this case, PZT is a perfect material for the detection of the impingement, since impingement is the collision between either bones or prosthetic joints. A bulk of metal and another bulk of hard wood of same size were erected as an obstacle on the trajectory of the test specimen to mimic prosthetic and bony impingement. As shown in FIG. 25, passive sensing was utilized for the detection of impingement. The large voltage peaks corresponded to time of an impact. With a value more than 10 times than the voltage of smooth movement between two articulation surfaces, the outstanding impact of the impingement can be easily picked up by passive sensing.

Surface Damage Testing:

Passive sensing was used for surface damage detection. Wear testing was performed for one million cycles with overflowing levels of lubricant. However, the data within the time range did not indicate any significant differences among each cycle. Furthermore, no changes in the surface condition were observed. On the other hand, the data collected after the joint was polished was distinguishable from the data collected when the joint was scratched. As shown in FIGS. 26A-26D, in comparison to the scratched surfaces, the polished ones have much a smoother signal. The results show a promising future of the application of passive sensing on surface damage detection. FIG. 26A shows the sensor signal of scratched surfaces; FIG. 26B shows the Power Spectral Density (PSD) of the scratched surfaces; FIG. 26C shows the sensor signal of polished surfaces; and FIG. 26D shows the PSD of the polished surfaces.

The Feasibility of PZT Based Active Sensing for the Fluid Thickness Detection

Static and dynamic testing was carried out using the active sensing based on PZT transducers for detecting the change in lubricant thickness in a hip resurfacing prosthesis. By comparing the measured data to the estimated lubricant thickness, it is clear that with the same lubricant, the amplitude of the sensor data shares the same variation tendency with the lubricant thickness. Moreover, for certain frequencies, the sensor signal is highly sensitive to the change in the lubricant thickness. As the thickness change from several nanometers to hundreds of nanometers, the amplitude rises from dozens of millivolts to several volts.

As the pendulum of the simulator swung, the loading varied according to the phase. Thus, with a proper amount of lubrication, in one cycle of the hydrodynamic motion, different positions of the surface can encounter a breakdown of lubrication, an excess of lubrication, etc. It was shown that the breakdown occurred more easily on the edge. With enough sensors mounted in different positions, the dynamic tests were able to measure the thickness of the lubrication along the direction the pendulum swings. Also, the measurement provided information on the dynamic distribution of the lubricant as the surface motion between the ball and the socket continued. The information can be helpful in analyzing the fluid mechanics of the lubricant.

Active Sensing on Lubrication Regime Identification:

The minimum thickness of the lubricant can be estimated by knowing the dimensions of the artificial joint, the loading profile, and the viscosity of the lubricant. Once the minimum lubricant thickness is estimated, the lambda ratio, which represents the corresponding lubrication regime, can then be calculated. Thus, the lubrication regimes identified by the PZT based active sensing was comparable to those detected by the estimation based on the approximation formulas. This illustrates the feasibility and effectiveness of the methods discussed herein.

The method used to determine the lubrication regime is innovative and efficient. By picking up the unique features of each regime, a solid diagnosis can be reached in a timely fashion. To further confirm the method, AMPA can be used.

Passive Sensing Using PZT:

Passive sensing was employed to detect stick-slip phenomenon, impingement and surface damages. According to equations 3-1 and 3-2, when PZT works as a sensor, the electricity generated is directly proportional to the strain applied to it. As the components of the simulator move and change orientation, the strain experienced by the PZT changes. When the pendulum changes its motion direction, a very large acceleration sometimes causes a peak in sensor signal. Such peaks could be a location or a phase indicator for the pendulum. Thus, the significance of the stick-slip phenomena in different lubrication regimes can be compared by identifying the time difference between the appearances of peaks.

PZT sensor shows great capability to capture vibration signals, especially vibration from collision. Such an advantage is ideal for picking up the occurrence of impingement. In addition, impingement sometimes occurs in mild contact situations which do not cause outstanding peaks in the signal of PZT sensor.

A comparison of the signals generated by scratched and polished surfaces shows that the PZT is promising in regards to the detection of surface damages.

Implementations described herein are included to demonstrate particular aspects of the present disclosure. It should be appreciated by those of skill in the art that the implementations described herein merely represent exemplary implementation of the disclosure. Those of ordinary skill in the art should, in light of the present disclosure, appreciate that many changes can be made in the specific implementations described and still obtain a like or similar result without departing from the spirit and scope of the present disclosure. From the foregoing description, one of ordinary skill in the art can easily ascertain the essential characteristics of this disclosure, and without departing from the spirit and scope thereof, can make various changes and modifications to adapt the disclosure to various usages and conditions. The implementations described hereinabove are meant to be illustrative only and should not be taken as limiting of the scope of the disclosure.

What is claimed is:

1. A method for monitoring a joint comprising:
positioning a first piezoelectric transducer in a first component of a joint, wherein the first piezoelectric transducer is configured to detect acoustic signals, and the first piezoelectric transducer has an operating frequency of 100 kHz to 300 kHz;
positioning a second piezoelectric transducer in a second component of the joint, wherein the first piezoelectric transducer and the second piezoelectric transducer are separated by a lubrication region;
applying a voltage to the second piezoelectric transducer, wherein the applied voltage causes the second piezoelectric transducer to generate desired acoustic signals emitted toward the first piezoelectric transducer;
monitoring, with a processor, the joint with the first piezoelectric transducer, wherein the first piezoelectric transducer detects active signals transmitted through the joint by the second piezoelectric transducer; and
analyzing the active signals, with the processor, to determine conditions of the joint, wherein the first piezoelectric transducer provides real-time dynamic monitoring of the joint, and said active signals are utilized, with the processor, to determine lubrication thickness or a lubrication regime,
where hydrodynamic lubrication is detected, with the processor, when a distribution of a voltage amplitude range of said active signals remains smooth and a minimum peak-to-peak amplitude of the voltage is at least ⅓ a maximum peak-to-peak amplitude of the voltage,
mixed lubrication is detected, with the processor, when the minimum peak-to-peak amplitude occasionally encounters sudden drops less than ¹⁄₂₀ the maximum peak-to-peak amplitude, and
boundary lubrication is detected, with the processor, when the distribution decreases in overall amplitude and the minimum peak-to-peak amplitude drops further below the ¹⁄₂₀ the maximum peak-to-peak amplitude indicating frequent contact between asperities.

2. The method of claim 1, wherein said first piezoelectric transducer or said second piezoelectric transducer is a lead zirconate titanate (PZT) transducer.

3. The method of claim 1, wherein the first piezoelectric transducer is positioned on or in a first articulating component of the joint.

4. The method of claim 3, wherein said first articulating component is a trochlear notch of an ulna, condyle of a tibia, acetabulum of a pelvis, or glenoid cavity of the scapula.

5. The method of claim 1, wherein the second piezoelectric transducer is positioned on or in a second articulating component of the joint.

6. The method of claim 5, wherein said second articulating component is a trochlea of a humerus, condyles of a femur, greater trochanter of a femur, or a humeral head of the humerus.

7. The method of claim 1, wherein the joint is a knee joint, elbow joint, shoulder joint, or temporo-mandibular joint.

8. The method of claim 1, wherein the first and second piezoelectric transducers operate in situ or in vivo.

9. The method of claim 1 further comprising monitoring the joint for passive signals, wherein said passive signals are utilized to detect stick-slip conditions, impingement, or surface damage in said joint.

10. The method of claim 1, wherein the minimum peak-to-peak amplitude of the voltage is monitored to detect lubrication breakdown.

11. A method for monitoring a joint comprising:
positioning first and second piezoelectric transducers respectively in a first component and a second component the joint, wherein the first piezoelectric transducer and the second piezoelectric transducer are separated by a lubrication region;
applying a voltage to the second piezoelectric transducer, wherein the applied voltage causes the second piezoelectric transducer to generate desired acoustic signals; and
detecting, by a processor, received acoustic signals at the first piezoelectric transducer, wherein the first piezoelectric transducer has an operating frequency of 100 kHz to 300 kHz, and the received acoustic signals are the desired acoustic signals after propagation through the joint from the second piezoelectric transducer to the first piezoelectric transducer, wherein the first piezoelectric transducer provides real-time dynamic monitoring of the joint, and said received signals are utilized, by the processor, to determine lubrication thickness or a lubrication regime,
where hydrodynamic lubrication is detected, by the processor, when a distribution of a voltage amplitude range of said active signals remains smooth and a minimum peak-to-peak amplitude of the voltage is at least ⅓ a maximum peak-to-peak amplitude of the voltage,
mixed lubrication is detected, by the processor, when the minimum peak-to-peak amplitude occasionally encounters sudden drops less than ¹⁄₂₀ the maximum peak-to-peak amplitude, and
boundary lubrication is detected, by the processor, when the distribution decreases in overall amplitude and the minimum peak-to-peak amplitude drops further below the ¹⁄₂₀ the maximum peak-to-peak amplitude indicating frequent contact between asperities.

12. The method of claim 11, further comprising:
monitoring the joint to detect passive signals generated by the joint; and
analyzing the passive signals to determine conditions of the joint.

13. The method of claim 11, wherein passive signals are utilized to detect stick-slip conditions, impingement, or surface damage in said joint.

14. The method of claim 11, wherein the minimum peak-to-peak amplitude of the voltage is monitored to detect lubrication breakdown.

* * * * *